United States Patent
Müller et al.

(10) Patent No.: US 8,663,692 B1
(45) Date of Patent: *Mar. 4, 2014

(54) LIPID PARTICLES ON THE BASIS OF MIXTURES OF LIQUID AND SOLID LIPIDS AND METHOD FOR PRODUCING SAME

(75) Inventors: Rainer H. Müller, Berlin (DE); Volkard Jenning, Berlin (DE); Karsten Mader, Berlin (DE); Andreas Lippacher, Berlin (DE)

(73) Assignee: Pharmasol GmbH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/959,732

(22) PCT Filed: May 8, 2000

(86) PCT No.: PCT/EP00/04112
§ 371 (c)(1),
(2), (4) Date: Mar. 18, 2002

(87) PCT Pub. No.: WO00/67728
PCT Pub. Date: Nov. 16, 2000

(30) Foreign Application Priority Data

| | | |
|---|---|---|
| May 7, 1999 | (DE) | 199 21 034 |
| Aug. 9, 1999 | (DE) | 199 38 371 |
| Sep. 21, 1999 | (DE) | 199 45 203 |
| Mar. 31, 2000 | (DE) | 100 16 357 |

(51) Int. Cl.
*A61K 9/14* (2006.01)
*A61K 9/16* (2006.01)
*A61K 8/02* (2006.01)

(52) U.S. Cl.
USPC .................. 424/489; 424/401; 424/498

(58) Field of Classification Search
USPC .................................. 424/489–502
See application file for complete search history.

(56) References Cited

U.S. PATENT DOCUMENTS

| | | | |
|---|---|---|---|
| 4,880,634 A | 11/1989 | Speiser | |
| 4,889,740 A * | 12/1989 | Price | 426/606 |
| 5,188,837 A | 2/1993 | Domb | |
| 5,250,236 A | 10/1993 | Gasco | |

(Continued)

FOREIGN PATENT DOCUMENTS

| | | |
|---|---|---|
| CA | 2278685 A1 | 8/1998 |
| CA | 2119253 A1 | 11/1998 |

(Continued)

OTHER PUBLICATIONS

Garti et al. Stabilization of water-in-oil emulsions by submicrocrystalline alpha-form fat particles. JAOCS 75(12), 1998, 1825-1831.*

(Continued)

*Primary Examiner* — Lakshmi Channavajjala
(74) *Attorney, Agent, or Firm* — Jeffrey S. Melcher; Manelli Selter PLLC

(57) ABSTRACT

The invention relates to drug-free or drug-loaded lipid particles of a mixed matrix made of solid and liquid lipids, and to a method for producing highly concentrated lipid particle dispersions of solid-liquid particles having a lipid content of from 30% to 95% or a solids content of from 30% to 95% (lipid and stabilizer), which in contrast to biamphipileic cremes are integer particles, and/or which upon dilution of the highly concentrated particle dispersions with the outer phase result in free-flowable particle dispersions.

63 Claims, 17 Drawing Sheets

(56) References Cited

U.S. PATENT DOCUMENTS

| | | | | |
|---|---|---|---|---|
| 5,665,379 | A | * | 9/1997 | Herslof et al. ............... 426/450 |
| 5,667,800 | A | * | 9/1997 | De Vringer ................... 424/450 |
| 5,785,976 | A | * | 7/1998 | Westesen et al. ............ 424/400 |
| 6,551,619 | B1 | * | 4/2003 | Penkler et al. ............... 424/489 |

FOREIGN PATENT DOCUMENTS

| | | | |
|---|---|---|---|
| DE | 19707309 A1 | | 8/1998 |
| DE | 19819273 A1 | | 11/1999 |
| EP | 0043254 A1 | * | 1/1982 |
| EP | 0167825 A1 | | 1/1986 |
| EP | 0448930 a1 | * | 2/1991 |
| EP | 0506197 A1 | | 9/1992 |
| EP | 0525307 A1 | * | 2/1993 |
| EP | 0605497 A1 | | 7/1994 |

OTHER PUBLICATIONS

Bunjes, Westesen, Koch, "Crystallization tendency and polymeric transitions in triglyceride nanoparticles," International Journal of Pharmaceutics, 129 (1996), pp. 159-173.

Morel, Thymopentin in Solid Lipid Nanoparticles, Int. J. Pharm., 259-261, 1996.

Freitas, Effect of Light and Temperature on Zeta Potential and Physical Stability in Solid Lipid Nanoparticle Dispersions, Int. J. Pharm., 221-229, 1998.

Muhlen, Solid Lipid Nanoparticles for Controlled Drug Delivery—Drug Release and Release Mechanism, Eur. J. Pharm. Biopharm. 45, 149, 1998.

Lukowski, Surface Investigation and Drug Release of Drug-Loaded Solid Lipid Nanoparticles, Proc. 2nd World Meeting APGI/APV, Paris, 573-574, 1998.

Freitas, Effect of Storage Conditions on Long-Term Stability of Solid Lipid Nanoparticles in Aqueous Dispersion, 1st World Meeting APGI/APV, Budapest, 493-494, 1995.

Zeidler, Pharmacy Archive 324, 1991, 687.

Hernqvist, Crystal Structures of Fats and Fatty Acids, in: Garti et al., Crystallisation and Polymorphism of Fats and Fatty Acids, Marcel Dekker Inc., New York, Basle, 97-138, 1988.

Schlichter, Solidification and Polymorphism in Cacoa Butter and the Blooming Problems, in Gard, Crystallisation and Polymorphism of Fats and Fatty Acids, Marcel Dekker Inc., New York, Basle, 363-392, 1988.

Yoshino, Influence of Fatty Acid Composition on the Properties and Polymorphic Transition of Fatty Suppository Bases, Chem. Pharm. Bull. 31, 237-246, 1983.

Westesen, Physicochemical Characterisation of Lipid Nanoparticles and Evaluation of their Drug Loading Capacity and Sustained Release Potential, J. Control. Release 48, 223-236, 1997.

Eldem, Optimization of Spray Dried and Congealed Lipid Micropellets and Characterisation of their Surface Morphology by Scanning Electron Microscopy, Pharm. Res. 8, 47-51, 1991.

Tsutsumi, J. Soc. Cosmet. Chem. 30, 345-356, 1979.

Freits C., Müller R.H., Correlation between long-term stability of solid lipid nanoparticles (SLN) and crystallinity of the lipid phase, Eur. J. Pharm. Biopharm., Mar. 1999;47(2):125-32.

Souto E. B., Anselmi C., Centini M., Muller R. H., Preparation and characterization of n-dodecyl-ferulate-loaded solid lipid nanoparticles (SLN), Int. J. Pharm., May 13, 2005;295(1-2):261-8.

FDA/Industry Activities Staff Booklet: 1992, Cosmetic Handbook, 2. *Cosmetic Good Manufacturing Practice Guidelines*, Guidelines 5.a.

Muller R. H., Radtke M., Wissing S. A., Solid Lipid nanoparticles (SLN) and nanostructured lipid carriers (NLC) in cosmetic and dermatological preparations, Adv. Drug. Deliv. Rev., Nov. 1, 2002;54 Suppl 1:S131-55.

Müller, R. H., Radtke, M., Wissing, S. A., Nanostructured lipid matrices for improved microencapsulation of drugs, Int. J. Pharm. 242, 121-128, 2002.

Muller R. H., Radtke M., Wissing S. A., Solid lipid nanopracticles (SLN) and nanostructured lipid carriers (NLC) in cosmetic and dermatological preparations, Adv. Drug. Deliv. Rev., Nov. 1, 2002;54 Suppl 1:S131-55.

Gershanik T., Benzeno S., Benita S., Interaction of a self-emulsifying lipid drug delivery system with the everted rat intestinal mucosa as a function of droplet size and surface charge, Pharm. Res., Jun. 1998;15(6):863-9.

Pinto, J. F., Muller, R. H., Pellets as carriers of solid lipid nanoparticles (SLN™) for oral administration of drugs, Die Pharmazie 54, 506-509 (1999).

Mayhew, E. et al., Characterization of liposomes prepared using a microemulsifyer, Biochimica et Biophysica Acta 775, 169-174 (1984).

Bunjes, H., Westesen, K., Koch, M. H. J., Crystallisation tendency and polymorphic transitions in triglyceride nanoparticles, Int. J. Pharm. 129, 159-173 (1996).

Saupe, A. et al., Solid lipid nanoparticles (SLN) and nanostructured lipid carriers (NLC) — structural investigations on two different carrier systems, Bio-Medical Materials and Engineering 15, 393-402 (2005).

* cited by examiner shell, α-modification

▼ solid bridge

Imwitor 1d

Imwitor 168d

2 Theta (°)

LIPID PARTICLES ON THE BASIS OF MIXTURES OF LIQUID AND SOLID LIPIDS AND METHOD FOR PRODUCING SAME

CROSS-REFERENCE TO RELATED APPLICATIONS

This application is a national stage entry under 35 U.S.C. 371 of International Application No. PCT/EP2000/04112, filed 8 May 2000, designating the United States. This application claims foreign priority under 35 U.S.C. 119 and 365 to German Patent Application Nos. 100 16 357.2, filed 31 Mar. 2000; 199 45 203.2, filed 21 Sep. 1999; 199 38 371.5, filed 9 Aug. 1999; and 199 21 034.9, filed 7 May 1999.

FIELD OF THE INVENTION

The invention relates to drug-free or drug-loaded lipid particles of a mixed matrix made of solid and liquid lipids, and to a method of making the lipid particles.

BACKGROUND OF THE INVENTION

Lipid particles of various sizes are employed for the controlled delivery of drugs. Hard gelatine capsules are filled with medicament-loaded lipid pellets with a size of approximately 0.10-2.0 mm, and the drug undergoes prolonged release from the lipid pellets, (commercial product Mucosolvan® [Müller, R. H., Feste Lipidnanopartikel [Solid lipid nanoparticles] (SLN), in Müller, R. H., Hildebrand, G. E. (eds.), Pharmazeutische Technologie: Moderne Arzneiformen [Pharmaceutical technology: modern dosage forms], Wissenschaftliche Verlagsgesellschaft Stuttgart, 357-366, 1998]). Lipid microparticles can be used for various application routes, from topical products (e.g. O/W creams) through oral medications to parenterals. An order of magnitude smaller are solid lipid nanoparticles (SLN®), which have an even wider range of use. Because of the fineness of the particle size, ophthalmological use is for example also possible.

Lipid particles can be employed in the form of a free-flowing dispersion, i.e. the lipid particles are dispersed in an aqueous phase (e.g. in isotonic glucose solution) or in a non-aqueous phase (e.g. in PEG 600 or oil). When used as a dispersion, the system must generally be free-flowing, i.e. of low viscosity. The lipid concentration in the dispersions is generally relatively low, in the range of approximately 1-100 (percent by weight). This is sufficient for most application purposes. If necessary, the lipid particle concentration may also be readily increased to up to 20% (similar to 20% oil containing emulsions for parenteral nutrition).

The situation regarding the required lipid concentration is different when incorporating lipid particles into traditional dosage forms such as creams, oral medicinal forms such as tablets, pellets or capsules, as well as in the case of parenterals with a limited injection volume. Substantially higher lipid concentrations are required here in order to reduce the proportion of water in the dispersion, which must be removed in order to produce the tablets, for example. This is true, in particular, when large amounts of lipid need to be incorporated into these medicinal forms, owing to the low medicament-loading capacity of the particles.

The incorporation of highly concentrated lipid particles into these medicinal forms is not difficult when relatively large particles are involved (>100 μm). The lipids can be ground to a coarse powder using a conventional mill. The particles thus obtained at a size of 100-200 μm are admixed as a powder in the production process of the dosage form.

The situation is more difficult with lipid microparticles and lipid nanoparticles. For lipid microparticles in the range of approximately 1-100 μm, highly energetic grinding is necessary in order to achieve this fineness of the particle size. The heat inevitably given off during the grinding process can partially melt the lipid and cause clumping; compensatory cooling is generally necessary. Fine powders, especially in the case of a hydrophobic surface, are susceptible to particle aggregation. In order to avoid this problem, wet grinding is essential, optionally with the addition of a surfactant. Highly fine lipid particles, i.e. in the range of a few micrometers and in particular in the nanometer range, cannot generally be produced by dry grinding. For wet grinding, the coarse lipid powder is dispersed in a liquid and is processed using an appropriate wet mill (e.g. colloid mill). Further possible modes of production include high pressure homogenisation methods [Müller, R. H., Feste Lipidnanopartikel (SLN), in Müller, R. H., Hildebrand, G. E. (eds.), Pharmazeutische Technologie: Moderne Arzneiformen, Wissenschaftliche Verlagsgesellschaft Stuttgart, 357-366, 1998] or alternatively precipitation [Morel, S., Ugazio, E., Cavalli, R., Gasco, M. R., Thymopentin in Solid Lipid Nanoparticles, Int. J. Pharm., 259-261, 1996]. Highly fine lipid particles can generally be incorporated into the aforementioned dosage forms only in the form of a dispersion.

Highly concentrated lipid particle dispersions are essential for the production of oral dosage forms and certain parenterals. For the production of tablets, for instance, the aqueous lipid particle dispersion is used as a granulating liquid. The volumes of aqueous lipid particle dispersion to be used for incorporating a particular amount of lipid particles as granulating liquid must not be too high, since otherwise too much water will need to be removed or granulation will no longer be even possible. Similar considerations apply to the use of aqueous lipid particle dispersions to make a paste of the excipient mixture for pellet extrusion. Soft gelatine capsules can be filled with non-aqueous lipid particle dispersions. When the lipid has a given maximum drug-loading capacity, the lipid particle dispersion must here also be sufficiently concentrated in terms of lipid particles in order not to exceed the maximum possible filling volume of the capsule.

This will be explained with reference to an example. The single dose of cyclosporin for adults is approximately 200 mg. The lipid nanoparticles produced by using cyclosporin have a maximum loading capacity of 20%, i.e. the lipid matrix consists of 200 mg of cyclosporin and 800 mg of lipid [Müller, R. H., Runge, S. A., Ravelli, V., Pharmazeutische Cyclosporin-formulierung mit verbesserten bio-pharmazeutischen Eigenschaften, erhöhter physikalischer Qualität and Stabillität sowie ein Verfahren zur Herstellung derselben [Pharmaceutical cyclosporin formulation with improved biopharmaceutical properties, higher physical quality and stability and a method for the production thereof], DE 198 19 273]. This single dose is to be administered in two tablets of 1 g each, i.e. 1 g of lipid/cyclosporin particles needs to be made into a paste with 1 g of excipients, for tabletting in the granulation process. At the current state of lipid nanoparticle production technology, 1 g of cyclosporin-loaded lipid nanoparticles is dispersed in 4 g of water (total volume of the aqueous lipid nanoparticle dispersion: approximately 5 ml=5 g). When mixing these 5 g with 1 g of tablet excipients, it is hence necessary to remove 4 g of water; 2 g of tablet mixture is obtained after the water is removed. It is clear that granulation is not possible with such low-concentration lipid nanoparticle dispersions (removal of 4 g of water from 6 g of granule mixture). Lipid particle dispersions with a lipid content of 50-70% are necessary. Similar problems are encountered in the case of a) drugs having on average a high single dose when incorporating drug-loaded lipid particles into any traditional dosage forms and b) drugs which, although they have a low single dose, are nevertheless difficult to incorporate into lipid particles (=low loading capacity).

SUMMARY OF THE INVENTION

The object of the invention was therefore to provide a production method for the production of highly concentrated lipid nanoparticle dispersions with a lipid content of from 30 to 95%, or a solids content (lipid+surfactant and/or stabiliser) of from 30 to 95%.

The production of lipid microparticle dispersions in the lower micrometer range is described in a number of patents, patent applications and in the literature. The maximum lipid concentrations used are, according to patent claims or examples, in this case e.g. 3% [Domb, A., Liposheres for controlled delivery of substances, U.S. Pat. No. 5,188,837, 1993], 30% [Gasco, M. R., Method for producing solid lipid microspheres having a narrow size distribution, U.S. Pat. No. 5,250,236, 1993] and 200 [Speiser, P., Lipidnanopellets als Trägersystem für Arzneimittel zur peroralen Anwendung [Lipid nanopellets as a carrier system for peroral administration of medicaments], European Patent EP 0 167 825, 1990]. For higher concentrations, the formation of gels (fat in water) or ointments (water dispersed in fat) is described. The maximum amounts of fat used for the production of lipid nanoparticles are 30% [Müller, R. H., Lucks, J. S., Arzneistoffträger aus festen Lipidteilchen [Medicament carriers consisting of solid lipid particles], Solid Lipid Nanospheres (SLN), European Patent EP 0 605 497, 1996]. Also in the case of lipid nanoparticles, the formation of lipid gels (O/W creams) is described when higher amounts of lipid are used [Freitas, C., Müller, R. H., Effect of light and temperature on zeta potential and physical stability in Solid Lipid Nanoparticle (SLN™) Dispersions, Int. J. Pharm., 221-229, 1998]. For the production of lipid nanoparticles by precipitation [Gasco, M. R., Method for producing solid lipid microspheres having a narrow size distribution, U.S. Pat. No. 5,250,236, 1993], a hot lipid microemulsion is added to a cold aqueous surfactant solution. This precipitation step necessarily leads to very dilute lipid nanoparticle dispersions. The maximum concentration obtainable in the aqueous dispersion is, according to the patent, 0.5-3% [Gasco, M. R., Method for producing solid lipid microspheres having a narrow size distribution, U.S. Pat. No. 5,250,236, 1993].

The object of the prior methods was to produce particle dispersions which were homogeneous in terms of size. Homogeneous particle dispersions are indeed emphasised in those patents which carry out the particle production by means of homogenisation methods. When dispersed in a homogenisation medium, however, homogeneous particles are susceptible to lining up in "pearl necklace" fashion and forming gels. The classical example is the gel formation of uniformly sized Aerosil particles, which occurs in both aqueous and non-aqueous media (e.g. oils) (FIG. 1). These pearl necklace-like gels are described in the textbooks [List, P. H., Arzneiformlehre [Teachings on medicinal forms], Wissenschaftliche Verlagsgesellschaft Stuttgart, p. 264, 1976]. Similar gel formation is, however, also described for particles which are relatively polydisperse owing to their production. The classical example of this are the bentonite gels described in the textbooks [List, P. H., Arzneiformlehre, Wissenschaftliche Verlagsgesellschaft Stuttgart, p. 264, 1976] (FIG. 2). The bonds within the gel framework of bentonite and Aerosil are not covalent, but purely electrostatic and/or hydrogen bridge bonds. Although there are no covalent bonds, the gel frameworks are relatively stable; even low concentrations lead to a highly viscous gel (e.g. 2% Aerosil in Miglyol 812). In the case of lipid nanoparticles, it has been found that they have a thin outer shell with a different structure from the particle core [after Mühlen, A., Schwarz, C., Mehnert, W., Solid Lipid Nanoparticles (SLN) for controlled drug delivery—Drug release and release mechanism, Eur. J. Pharm. Biopharm. 45, 149, 1998, Lukowski, G., Werner, U., Pflegel, P., Surface investigation and drug release of drug-loaded solid lipid nanoparticles, Proc. $2^{nd}$ World Meeting APGI/APV, Paris, 573-574, 1998]. When particles come into contact with one another, liquid crystalline $\alpha$ modification is converted into solid $\beta$ modification, lipid solid bridges are formed and particle aggregates result (FIG. 3). As the particle aggregation continues, a highly solid gel is formed [Freitas, C., Müller, R. H., Correlation between long-term stability of solid lipid nanoparticles (SLN™) and crystallinity of the lipid phase, Eur. J. Pharm. Biopharm. 47, 125-132, 1999]. It has been found that this gelling and gel formation process is commensurately stronger if the concentration of lipid particles is higher. The lipid particle concentrations investigated were relatively low at 0.1%-10% [Freitas, C., Müller, R. H., Correlation between long-term stability of solid lipid nanoparticles (SLN™) and crystallinity of the lipid phase, Eur. J. Pharm. Biopharm. 47, 125-132, 1999, Freitas, C., Lucks, J. S., Müller, R. H., Effect of storage conditions on long-term stability of "Solid Lipid Nanoparticles" (SLN) in aqueous dispersion, $1^{st}$ World Meeting APGI/APV, Budapest, 493-494, 1995]. During gel formation, lipid particles additionally become quasi-"glued" via lipid solid bridges.

In view of the above-described gel formation phenomena of monodisperse and polydisperse particles, the mechanism of solid bridge formation in the case of highly fine lipid particles and the fast transition rate from $\alpha$ modification into $\beta$ modification, i.e. within minutes e.g. in the case of hard fat [Sucker, H., Fuchs, P., Speiser, P., Pharmazeutische Technologie [Pharmaceutical Technology], Georg Thieme Verlag Stuttgart, 1978, Bauer, K. H., Framing, K.-H., Führer, C., Pharmazeutische Technologie [Pharmaceutical Technology], G. Fischer Verlag Stuttgart, p. 276, 1997], the production of highly concentrated lipid dispersions at a size of a few micrometers and, in particular, nanometers seemed unfeasible. Surprisingly, however, it has been found that a 40% concentrated high pressure homogenised lipid dispersion contained separate nanoparticles (Example 1). Even when the lipid content is increased further to 50%, it was still possible to obtain separate nanoparticles (Example 2). To produce lipid particles in the upper nanometer range or lower micrometer range, a rotor-stator (Ultra-Turrax, Janke & Kunkel, Germany) was used as a dispersing system with lower power density (Example 3). The production of lipid particle dispersions of uniform particle size (monodisperse) with a solid content significantly above 74% is physically impossible. With the densest spherical packing, the solids volume is 74% and that of the pores in between (the water phase in the case of lipid particle dispersions) is 24%. In order to enable denser packing, lipid particle dispersions of non-uniform particle size were therefore deliberately produced. To that end, contrary to conventional wisdom and teaching, suboptimal dispersing conditions (low pressure) or suboptimal dispersing devices (non-uniform power-density distribution) were deliberately used (Example 4). The production conditions and production devices used were precisely the opposite of those which are recommended in the literature for the production of lipid particle dispersions. Non-uniform size allows denser packing for the same distance between the particles, since smaller particles can fit into the gaps between larger particles, whereas the particle integrity is nevertheless surprisingly preserved.

The solids concentration of the lipid particle dispersions described in this invention is in the range of from 30% up to 95%. As the solids content increases, the production conditions need to become more suboptimal, i.e. the particle dispersion produced needs to become more polydisperse. In the upper concentration range, it is also necessary to add the lipid phase thereto successively in several steps. The stepwise added lipid fraction becomes finely dispersed in the water phase in the presence of lipid nanoparticles already present. After the dispersion and conversion into lipid nanoparticles has been completed, a further lipid fraction is added. For instance, when producing 100 g of an 80% lipid particle dispersion, instead of directly adding 80 g of lipid to 20 g of water, 20 g of lipid may be first introduced into 20 g of water (=50% strength dispersion) and a further 10 g of lipid may then be added in each of 6 further sub-steps. Each step therefore involves the dispersion of 10 g of lipid in 20 g of water and automatically, owing to the volume proportions, the formation of an O/W system.

The lipid may be dispersed in the outer phase either in the solid state (cold homogenisation) or in the liquid state (hot homogenisation). In the case of cold homogenisation, the lipid is dispersed in an aqueous surfactant solution (raw dispersion) and then treated further using a suitable device. In the case of hot homogenisation, the lipid is melted and poured into the outer phase, which is heated to the same temperature, and dispersed therein (raw emulsion). The raw emulsion obtained is then processed using a further dispersion device. Depending on the desired degree of dispersion, the concentration of the lipid phase and the aggregate state of the lipid, the following may be used as dispersion systems: high-pressure homogenisers of the piston-gap homogeniser type (APV Gaulin systems, French Press), jet-stream homogenisers (e.g. microfluidisers), rotor-stator systems (Ultra-Turrax, Silverson homogenisers) and static blenders on the micro-scale or macro-scale (e.g. Sulzer, Switzerland).

In particular in the case of dispersing highly concentrated molten lipids (hot homogenisation), it has been assumed that the typical biamphiphilic cream structures described in the textbooks are formed [Bauer, K. H., Frömming, K.-H., Führer, C., Pharmazeutische Technologie, G. Fischer Verlag Stuttgart, p. 276, 1997] (FIG. 4). From such structures, it is no longer possible to obtain particles such as e.g. nanoparticles. In the present invention, however, integer particles were surprisingly obtained even at a high lipid concentration.

Additives may be used to promote the formation of particles while minimising particle aggregates. Such additives are substances which shift the pH (e.g. increasing the zeta potential, influencing the surfactant structure and degree of dissociation) or deliberately increase the particle charge (e.g. anti-flocculants such as sodium citrate). Such additives can also increase the stability of the lipid particle dispersion, e.g. by influencing the water structure (e.g. electrolytes) or by effects on the stabilising surfactant layer (e.g. glucose in the case of lecithin).

The lipid particles may be loaded with active agents. Examples of active agents include drugs, cosmetic active agents, agricultural pesticides, food additives, chemical substances of various types (e.g. wood preservatives).

The loading with active agents may be carried out in various ways, individually or in combination. The active agent or agents are dissolved, solubilised (e.g. using surfactants or cyclodextrins) or dispersed in the lipid particles. Further they can be adsorbed at the surface of the particles. Because of their solid nature, it is also possible to incorporate hydrophilic active agents into the lipid phase in the form of an aqueous active-agent solution. This incorporation and the subsequent dispersion of the lipid in the aqueous dispersion medium results in a W/F/W system, i.e. water in fat in water. Because of its solid aggregate state, the lipoid core in this case encloses the aqueous drug solution better than is possible with comparable multiple water in oil in water (W/O/W) emulsions.

DETAILED DESCRIPTION OF THE INVENTION

The lipid particles according to the invention may be produced in the following way:
1. Dispersing the inner phase (the lipid or lipoid) in the molten or softened state. The dispersion takes place above room temperature and may be carried out using various methods, for example the ones described below.
2. Dispersing the solid inner phase in the solid state. The solid phase is for this purpose finely comminuted and dispersed in water or in an aqueous medium.

The dispersed lipid core, which is solid at room temperature, has been loaded beforehand with one or more active agents. This may be done by dissolving or dispersing the active agent in the lipid, or adsorbing it on the surface, or dispersing it in the lipid in the form of an aqueous solution or simultaneously incorporating it using several of these methods.

The incorporation of the active agent or agents may be carried out using various methods. Examples include:
1. Dissolving the active agent in the inner phase.
2. Dissolving the active agent in a solvent which is miscible with the inner phase and adding this active-agent solution to the inner phase. Optionally, the solvent may then be partially or completely removed.
3. Dispersing the active agent in the inner phase (e.g. by dispersing a solid or controlled precipitation).
4. Dissolving the active agent in the outer aqueous phase (e.g. amphiphilic substances) and incorporating the active agent into a surfactant film which stabilises the particles, during production.
5. Adsorbing the active agent on the particle surface.
6. Dissolving the active agent in the lipid phase by means of a solubiliser (e.g. a block copolymer or fatty acid sorbate), and subsequently dispersing the lipid phase in order to produce the raw dispersion. The active agent is then present as a solid solution in the particles.
7. Incorporating aqueous active-agent solutions into the lipid phase and subsequently dispersing the lipid phase in order to produce the raw dispersion, so as to create a W/F/W system which is similar to multiple emulsions.

Active agents e.g. from the following chemical compound classes may be incorporated:
hydroxylated hydrocarbons
carbonyl compounds such as ketones (e.g. halopedol), monosaccharides, disaccharides and amino-sugars
carboxylic acids such as aliphatic carboxylic acids, esters of aliphatic and aromatic carboxylic acids, basically substituted esters of aliphatic and aromatic carboxylic acids (e.g. atropine, scopolamine), lactones (e.g. erythromycin), amides and imides of aliphatic carboxylic acids, amino acids, aliphatic aminocarboxylic acids, peptides (e.g. cyclosporin), polypeptides, β-lactam derivatives, penicillins, cephalosporins, aromatic carboxylic acids (e.g. acetylsalicylic acid), amides of aromatic carboxylic acids, vinylogous carboxylic acids and vinylogous carboxylates carbonic acid derivatives such as urethanes and thiourethanes, urea and urea derivatives, guanidine derivatives, hydantoins, barbiturate derivatives and thiobarbiturate derivatives nitro compounds such as aromatic nitro compounds and heteroaromatic nitro compounds amines such as aliphatic amines, aminoglycosides, phenylalkylamines, ephedrine derivatives, aromatic amines and derivatives, quaternary ammonium compounds sulphur compounds such as thiols and disulphanes sulphones, sulphonates and sulphonic acid amides polycarbocycles such as tetracyclines, steroids with an aromatic A ring, steroids with an alpha, beta-unsaturated carbonyl function in the A ring and an alpha ketol group (or methylketo group) at C 17, steroids with a butenolide ring at C 17, steroids with a pentadienolide ring at C 17 and secosteroids O-containing heterocycles such as chromane derivatives (e.g. cromoglycic acid)

N-containing heterocycles such as pyrazole derivatives (e.g. propyphenazone, phenylbutazone)

imidazole derivatives (e.g. histamine, pilocarpine), pyridine derivatives (e.g. pyridoxine, nicotinic acid), pyrimidine derivatives (e.g. trimethoprim), indole derivatives (e.g. indomethacin), lysergic acid derivatives (e.g. ergotamine), yohimbane derivatives, pyrrolidine derivatives, purine derivatives (e.g. allopurinol), xanthine derivatives, 8-hydroxyquinoline derivatives, aminohydroxyalkylated quinolines, aminoquinolines, isoquinoline derivatives (e.g. morphine, codeine), quinazoline derivatives, benzopyridazine derivatives, pteridine derivatives (e.g. methotrexate), 1,4-benzodiazepine derivatives, tricyclic N-containing heterocycles, acridine derivatives (e.g. ethacridine) and dibenzazepine derivatives (e.g. trimipramine)

S-containing heterocycles such as thioxanthene derivatives (e.g. chlorprothixene)

N,O-containing and N,S-containing heterocycles such as monocyclic N,O-containing heterocycles, monocyclic N,S-containing heterocycles, thiadiazine derivatives, bicyclic N,S-containing heterocycles, benzothiadiazine derivatives, tricyclic N,S-containing heterocycles and phenothiadiazine derivatives O,P,N-containing heterocycles (e.g. cyclophosphamide).

In particular, the following groups and substances may be incorporated as medicaments, e.g. as a salt, ester, ether or in the free form:

Analgesics/Antirheumatics
  BTM bases such as morphine, codeine, piritramide, fentanyl and fentanyl derivatives, levomethadone, tramadol, diclofenac, ibuprofen, naproxen, piroxicam, penicillamine Antiallergics
  pheniramine, dimethindene, terfenadine, astemizole, loratidine, doxylamine, meclozine, bamipine, clemastine Antibiotics/Chemotherapeutics
  of these: polypeptide antibiotics such as colistin, polymyxin B, teicplanin, vancomycin; antimalarials such as quinine, halofantrine, mefloquine, chloroquine, virustatics such as ganciclovir, foscarnet, zidovudine, aciclovir and others such as dapsone, fosfomycin, fusafungin, trimethoprim Antiepileptics
  phenyloin, mesuximide, ethosuximide, primidone, phenobarbital, valproic acid, carbamazepine, clonazepam Antimycotics
  a) internal:
    nystatin, natamycin, amphotericin B, flucytosine, miconazole, fluconazole, itraconazole
  b) external furthermore:
    clotrimazole, econazole, tioconazole, fenticonazole, bifonazole, oxiconazole, ketoconazole, isoconazole, tolnaftate Corticoids (Internals)
  aldosterone, fludrocortisone, betamethasone, dexamethasone, triamcinolone, fluocortolone, hydroxycortisone, prednisolone, prednylidene, cloprednol methylprednisolone Dermatics
  a) Antibiotics:
    tetracycline, erythromycin, neomycin, gentamicin, clindamycin, framycetin, tyrothricin, chlortetracycline, mipirocin, fusidic acid
  b) Virustatics as above, furthermore:
    podophyllotoxin, vidarabine, tromantadine
  c) Corticoids as above, furthermore:
    amcinonide, fluprednidene, alclomethasone, clobetasol, diflorasone, halcinonide, fluocinolone, clocortolone, flumethasone, diflucortolone, fludroxycortide, halomethasone, desoximethasone, fluocinonide, fluocortinbutyl, fluprednidene, prednicarbate, desonide Diagnostics
  a) radioactive isotopes such as Te99m, In111 or I131, covalently bonded to lipids or lipoids or other molecules or in complexes
  b) highly substituted iodine compounds such as e.g. lipids Haemostyptics/Antihaemorrhagics
  blood-clotting factors VIII, IX Hypnotics, Sedatives
  cyclobarbital, pentobarbital, phenobarbital, methaqualone (BTM), benzodiazepines (flurazepam, midazolam, nitrazepam, lormetazepam, flunitrazepam, triazolam, brotizolam, temazepam, loprazolam)

Hypophyseal, Hypothalamic Hormones, Regulator Peptides and Their Inhibitors
  corticotrophin, tetracosactide, chorionic gonadotropin, urofollitropin, urogonadotropin, somatropin, metergoline, bromocriptine, terlipressin, desmopressin, oxytocin, argipressin, ornipressin, leuprorelin, triptorelin, gonadorelin, buserelin, nafarelin, goselerin, somatostatin Immunotherapeutics and Cytokines
  dimepranol-4-acetatamidobenzoate, thymopentin, α-interferon, β-interferon, γ-interferon, filgrastim, interleukins, azathioprine, cyclosporine Local Anaesthetics
  internal:
    butanilicaine, mepivacaine, bupivacaine, etidocaine, lidocaine, articaine, prilocalne
  external furthermore:
    propipocaine, oxybuprocaine, tetracaine, benzocaine Antimigraines
  proxibarbal, lisuride, methysergide, dihydroergotamine, clonidine, ergotamine, pizotifen Narcotics
  methohexital, propofol, etomidate, ketamine, alfentanil, thiopental, droperidol, fentanyl Parathyroid Hormones, Calcium Metabolism Regulators
  dihydrotachysterol, calcitonin, clodronic acid, etidronic acid Ophthalmics
  atropine, cyclodrine, cyclopentolate, homatropine, tropicamide, scopolamine, pholedrine, edoxudine, idouridine, tromantadine, acyclovir, acetazolamide, diclofenamide, carteolol, timolol, metipranolol, betaxolol, bupranolol, levobununol, carbachol, pilocarpine, clonidine, neostigmine Psychopharmaceuticals
benzodiazepines (lorazepam, diazepam), clomethiazol Thyroid Therapeutics
1-thyroxine, carbimazole, thiamazole, propylthiouracil Sera, Immunoglobulins, Inocula
a) immunoglobulins generally and specifically, such as hepatitis types, rubella, cytomegalovirus, rabies, FSME, chickenpox, tetanus, rhesus factors
b) immunosera such as botulism antitoxin, diphtheria, gas gangrene, snake venom, scorpion venom
c) inocula such as influenza, tuberculosis, cholera, diphtheria, hepatitis types, FSME, rubella, haemophilus influenzae, measles, neisseria, mumps, poliomyelitis, tetanus, rabies, typhus Sex Hormones and their Inhibitors
anabolics, androgens, antiandrogens, gestagens, oestrogens, antioestrogens (tamoxifen etc.)

Cytostatics and Metastasis Inhibitors
a) alkylating agents such as nimustine, melphalan, carmustine, lomustine, cyclophosphamide, ifosfamide, trofosfamide, chlorambucil, busulphan, treosulphan, prednimustine, thiotepa
b) antimetabolites such as cytarabine, fluorouracil, methotrexate, mercaptopurine, thioguanine
c) alkaloids such as vinblastine, vincristine, vindesine
d) antibiotics such as aclarubicin, bleomycin, dactinomycin, daunorubicin, doxorubicin, epirubicin, idarubicin, mitomycin, plicamycin
e) complexes of B group elements (e.g. Ti, Zr, V, Nb, Ta, Mo, W, Ru, Pt) such as carboplatin, cisplatin and metallocene compounds such as titanocene dichloride
f) amsacrine, dacarbazine, estramustine, etoposide, hydroxycarbamide, mitoxantrone, procarbazine, temiposide
g) alkylamidophospholipids (described in J. M. Zeidler, F. Emling, W. Zimmermann and H. J. Roth, Archiv der Pharmazie [Pharmacy Archive], 324 (1991), 687)
h) ether lipids such as hexadecylphosphocholine, ilmofosine and the like, described in R. Zeisig, D. Arndt and H. Brachwitz, Pharmazie [Pharmacy] 45 (1990), 809-818.
i) taxans such as e.g. paclitaxel As mentioned above, the concentrated lipid particle dispersions are especially suitable because of their low water content for the production of various dosage forms such as e.g. granules (e.g. for filling sachets), tablets, pellets, capsules, dry products such as lyophilisates and spray-dried products. The essential advantage is that only small amounts of water need to be removed. This reduces the process time, costs and above all, because of the shorter process time, there is also less aggregation of particles.

Furthermore, because of the already sufficiently high viscosity, the concentrated lipid particle dispersions may be used directly as a topical medicinal form (e.g. gel) or after the addition of viscosity-increasing substances or a liquid oily phase.

The dispersions may, optionally after dilution with water, be sprayed using commercially available devices (e.g. nasal application) or atomised as an aerosol, e.g. using a Pariboy (Example 9) or HaloLite™ (Medic-Aid, England). A further possible use is for the production of parenteral medicinal forms, in particular if the volume to be applied is to be kept minimal. Because of the high concentration of lipid particles, small volumes can be implemented. The lipid particles can be produced aseptically or subsequently sterilised using standard methods.

Further active agents for incorporation into the lipid particles according to the invention are any type of odoriferous substances of natural, synthetic or semi-synthetic origin. Examples which may be used include essential oils such as citrus oil (Example 18), rose oil, lavender oil, bergamot oil, balm oil, clove oil, cinnamon oil, orange oil, jasmine oil, rosemary oil, aniseed oil, peppermint oil, sandalwood oil or ylang-ylang oil, their isolated constituents such as e.g. 1,8-cineole, menthol, terpin hydrate, limonene, α-pinene, eugenol and perfumes, in particular perfume oils. All perfumes available on the market may be used, e.g. Allure (Example 19), Coco, Egoiste, Chanel Nos 5, 19, 22 by Chanel, Miss Dior, Dune, Diorissime or Fahrenheit by Dior, Roma, Laura, Venezia by Laura Biagotti, L'air du temps by Nina Ricci, Chalimar by Guerlain, Tresor by Lancome, Gio by Armani, Escape, Obsession, CK One, CK be, Eternity by Calvin Klein, Berlin, Joop, Rococo, All about Eve, What about Adam, Nightflight by Joop, KL, Lagerfeld, Jako by Karl Lagerfeld, Extreme by Bulgari.

Besides odoriferous substances with a pleasant scent, it is also possible to incorporate odoriferous substances with a repulsive effect, e.g. repellents. Odoriferous substances with a repulsive effect may be incorporated e.g. as warning substances (protection against taking the product orally by mistake) or as repellents, e.g. against insects. Examples of natural repellents include citrus oils, eucalyptus oil and camphor, and examples of synthetic repellents include N,N-diethyltoluamide (DEET), dibutyl phthalate, dimethyl phthalate, 2-ethyl-1,3-hexanediol.

Further odoriferous substances include the so-called attractants such as e.g. pheromones. Lipid particles with attractants may e.g. be employed in cosmetics or in insecticides. Examples of pheromones include androstenone and androstenol; human pheromones are in particular used.

For insecticidal use or for killing small animals (e.g. fleas, lice), the lipid particles may also contain poisons as an active agent in addition to attractants. As an alternative, attractant-containing lipid particles may be mixed with lipid particles which contain poisons. Besides poisons which need to be taken orally by the insect/small animal, contact poisons may also be used. Because of their lipophilic nature, e.g. the lipid particles adhere to the lipophilic chitin exoskeleton of insects, and the contact poison can diffuse from the adhering particles into the insect. Examples of poisons include chlorinated hydrocarbons such as γ-hexachlorocyclohexane, pyrethrins, pyrethroids, alkyl phosphates such as paraoxon, parathion, fenthion, dichlorvos and carbamates such as butoxycarboxim, bendiocarb, methomyl, proxopur.

When oily odoriferous substances are incorporated, these oils represent the liquid lipid component in the lipid particles, that is to say the liquid odoriferous substance is mixed with a lipid which is solid at room temperature, and in addition one or more liquid lipids may also be added. Odoriferous substances may also be dissolved in a liquid lipid and subsequently blended with a solid lipid in order to produce a particle. Dissolving in the molten solid lipid is also possible as an alternative.

By incorporating the odoriferous substances into the lipid particles, it is possible to control their release, and prolonged release can in particular be achieved in a controlled way. For instance, products based on emulsions (oily odoriferous substances emulsified in water, odoriferous substances dissolved in the oil phase of an O/W emulsion) release the odoriferous substance relatively quickly. The product loses its odoriferous effect. Incorporation into the lipid particles reduces the discharge of odoriferous substances and hence prolongs the product efficacy (Examples 18 and 19).

Application examples for pleasant odoriferous substances include cosmetic products (lotions, aftershaves etc.), pharmaceutical products (increasing acceptance among patients) and products for the hygiene and sanitary sectors (e.g. scenting rooms for a prolonged period).

Further active agents for incorporation into the lipid particles according to the invention include the various types of markers (labels). Examples of such marking substances include radioactive substances, for example iodated lipids (iodated e.g. with iodine 131, iodine 123) and lipophilic indium compounds (e.g. indium-111 oxine (8-hydroxyquinoline)) and technetium 99m, which are molecularly bound or complexed or adsorbed. Such particles may be used for gamma scintigraphy, e.g. after intravenous injection for scintiography of the bone marrow and liver. Other markers include coloured substances (dyes) or fluorescent substances (fluorescent dyes).

An example of a coloured substance is Sudan red. Examples of fluorescent substances include Nile red and fluorescein. In general, lipid particles provided with markers may be used for both in vitro diagnosis and in vivo diagnosis. Examples of in vitro diagnosis include the characterisation of cell lines e.g. determination of the phagocytotic activity after differentiation of a cell line into a macrophage line. These particles may also be used in diagnostic kits. Examples of in vivo diagnosis include the marking of lymph nodes. For this purpose, the particles are injected close to lymph nodes; drainage into the lymph nodes and dyeing then take place. A further example is the marking of body cavities and analysis using fluorescence spectroscopy.

The lipid particles according to the invention may also be used without the incorporation of active agents as diagnostics in magnetic resonance (MR) tomography. Although the introduction of magnetic resonance tomography has made it possible to improve greatly diagnostic abdominal imaging, reliably distinguishing the gastrointestinal tract from normal or pathological surrounding tissue is even today often difficult or impossible. MR images are in principle possible without a contrast medium, but the signal intensities and therefore the strength of the contrast are improved by T1 and T2 contrast media, which influence the relaxation time. In order make the tissue structures more easily distinguishable, various substances have been proposed as contrast media. In principle, they may in this regard to be divided into negative contrast media (magnetites) and positive contrast media (e.g. Magnevist). All substances tested to date can only satisfy the requirement catalogue (low price, good acceptance and toleration, lack of toxicity, no inducing of motion artefacts, resistance to pH, homogeneous distribution throughout the gastrointestinal tract, good contact with the intestinal wall, contrast provision in all pulse sequences) to a limited extent. Owing to their high fat content, SLNs are oral T1 MR contrast media. The advantages are low price, good acceptance (taste, tolerability), toleration, lack of toxicity (physiological lipids), homogeneous distribution in the gastrointestinal tract and good coverage of the intestinal wall (particle size).

Of the SLN dispersions tested using a Bruker minispec pc120, e.g. Witepsol H15 (C12-C18 hard fat) and Witepsol E85 (C12-C18 hard fat) are suitable as MR contrast media because of their influence on the T1 relaxation times.

It is also possible to incorporate magnetites ($Fe_2O_3$, iron oxides) into the lipid particles according to the invention as markers. In particular, small iron oxide particles in the range of approximately 1 to 3 nm are incorporated into the lipid matrix. They can also be used as a contrast medium for magnetic resonance tomography.

The above-described conversion of lipids of the lipid particle matrix into the highly ordered stable β modification leads to physical destabilisation, i.e. to particle aggregates (via e.g. solid bridge formation). This is prevented in the liquid/solid particles according to the invention in that a part of the lipid is in a highly disordered state, i.e. liquid state/melt (e.g. Miglyol, Example 12) or in a de facto liquid state (α modification). The α modification has a low packing density (K. Thoma, P. Serno, D. Precht, Röntgendiffraktometrischer Nachweis der Polymorphie von Hartfett [X-ray diffractometric investigation of the polymorphism of hard fat], Pharm. Ind. 45, 420-425, 1983); the fatty acid residues can oscillate relatively freely, so that the state is similar to a melt (L. Hernqvist, Crystal structures of fats and fatty acids, in: N. Garti, K. Sato, Crystallisation and polymorphism of fats and fatty acids, Marcel Dekker Inc., New York, Basle, 97-138, 1988).

The invention also uses the fact that, in fats of complex composition (e.g. hard fat), a certain fraction is in the liquid form even below the melting point (I. Hassan, Phasenverhalten langkettiger Glyceride [Phase behaviour of long-chain glycerides], Phd thesis, Christian Albrecht University Kiel, 1988). The previous problem was, however, that this liquid fraction promotes the conversion of the metastable into the stable β modification (J. Schlichter-Aronhime, N. Garti, Solidification and polymorphism in cacoa butter and the blooming problems, in N. Garti, K. Sato, Crystallisation and polymorphism of fats and fatty acids, Marcel Dekker Inc., New York, Basle, 363-392, 1988; H. Yoshino, M. Kobayashi, M. Samejima, Influence of fatty acid composition on the properties and polymorphic transition of fatty suppository bases, Chem. Pharm. Bull. 31, 237-246, 1983). In the present invention, it was surprisingly found that a) this transition does not occur with an appropriate composition of the particle formulation (e.g. Example 13) or
b) occurs faster (Examples 14-16) with a certain composition of the particle formulation, which according to the invention can be employed for the controlled release of active agents.

The formation of the stable βi/β modification leads to the undesired effect that the active agents incorporated into the particle matrix become displaced (so-called drug exclusion). Active-agent crystals form in the lipid particle dispersions. On transition from the disordered state (liquid or liquid-like a modification) into the more stable βi/β modification, the number of liquid regions with dissolved drug is decreased, together with the number of lattice defects (and therefore the possibility of accommodating active-agent molecules in the lipid matrix). Perfect crystals are formed and the active agent becomes excluded. This is particularly pronounced in the case of pure monoacid triglycerides, which form highly crystalline solid lipid particles (Westesen, K., Bunjes, H., Koch, M. H. J., Physicochemical characterisation of lipid nanoparticles and evaluation of their drug loading capacity and sustained release potential, J. Control. Release 48, 223-236, 1997).

The solid/liquid lipid particles according to the invention remain even in highly concentrated dispersions as individual particles; after production (e.g. Example 6) and even after storage they have a liquid or a fraction (Example 13). The liquid fraction can be deliberately increased by adding liquid lipids (oils, e.g. triglycerides such as Miglyols) to solid lipids. Small amounts of oil can be dissolved in the solid lipid (i.e. distributed in molecularly dispersed form). When the oil solubility in the solid lipid is exceeded, undissolved oil molecules accumulate and compartments with liquid oil in the nanometer range are formed (so-called nano-compartments). Besides defects in the lipid lattice of a less perfect β' modification, active agent can here be incorporated in dissolved form in the liquid nano-compartments. A carrier is hence created, which consists of a solid lipid matrix with incorporated nano-compartments of liquid lipid, the nano-compartment carrier (NCC). Keeping as much lipid as possible in disordered form in this nano-compartment carrier and inhibiting the formation of βi/β modification (i.e. avoiding the formation of a solid lipid nanoparticle) promotes the active-agent incorporation.

Through mixing liquid and solid lipids, the particles according to the invention obtain a special internal structure with increased disorder (liquid compartments, liquid crystalline fractions, amorphous structures) and are no longer completely crystalline.

The crystallinity of the particles is measured by comparing their enthalpy of melting with the enthalpy of melting of the bulk material of the solid lipid which is used, when it is in its crystalline storage-stabilised modification, the β form (=100% crystallinity). The enthalpy of melting of the particles according to the invention is determined immediately after production using differential scanning calorimetry (DSC) in comparison with the bulk material. Calculating the enthalpy of melting of the particles as a percentage of the enthalpy of melting of the bulk material gives the crystallinity in percent, or the crystallinity index (e.g. 80% crystallinity corresponds to 0.80 on the crystallinity index, see below).

Particles with a crystallinity index of 1.0 are completely crystalline, particles with a crystallinity index of 0.50 or higher are predominantly crystalline. Predominantly non-crystalline particles have a crystallinity index of 0.50 or less; in the case of almost completely x-ray amorphous lipid particles, the crystallinity index tends to zero. Predominantly crystalline particles and predominantly non-crystalline particles are all partially crystalline, since at least a part of the matrix is crystalline.

It is possible to inhibit the formation of the stable $β_i/β$ modification in that—as explained above—disordered lipid (=without solid, highly ordered crystal structure) is present in partially crystalline particles because of a liquid fraction. Liquid lipids are mixed with solid lipids, in most cases the liquid fraction being less than 500. As an alternative, the required lack of crystallinity may also be created by deliberate production of amorphous particles. Amorphous structures show no crystallinity. The particles are formed when, as described above, a liquid lipid and a solid lipid are mixed, the fraction of the liquid lipid for forming these particles being generally at least 50%, possibly rising to 99%. The oil is quasi-solidified while avoiding the formation of an ordered crystalline structure. The particles formed are therefore likewise partially crystalline (predominantly non-crystalline), semi-solid to solid and x-ray amorphous at a temperature of 21° C.

These particles are therefore unlike the lipid particles described in the literature, which are produced
a) solely from solid lipids or
b) particles which are predominantly crystalline.

Eldem et al. (Eldem, T. et al., Optimization of spray dried and congealed lipid micropellets and characterisation of their surface morphology by scanning electron microscopy, Pharm. Res. 8, 47-51, 1991) disclose microparticles consisting of solid lipids, which are produced by spray-drying or spray-congealing. The matrix material of these particles consists exclusively of solid lipids. U.S. Pat. No. 5,188,837 (Domb A., Liposphere for controlled delivery of substances, 1993) describes lipid microspheres which consist of solid lipid (e.g. a wax) and are covered with a phospholipid layer. Tsutsumi et al. (J. Soc. Cosmet. Chem. 30, 345-356, 1979) describe crystalline microparticles of hard paraffin which, however, are physically unstable. Only as nanoparticles can sufficient physical stability of these hard-paraffin particles be obtained (de Vringer, T., Topical preparations containing a suspension of solid lipid particles, European patent application 0 506 197 A1, 1992). These and other nano- or microparticles of lipids are always predominantly crystalline (e.g. in the α or β' crystal modification). Because of the crystallinity of these particles, the take-up capacity for active agents is usually limited (Westesen, K., et al., Physicochemical characterisation of lipid nanoparticles and evaluation of their drug loading capacity and sustained release potential, J. Control. Rel. 48, 223-236, 1997).

The mixing of liquid and solid lipids leads to disordered structures with improved active-agent incorporation,
a) in the case of a liquid lipid fraction (oil) below 50%, predominantly disordered liquid regions (nano-compartments) being formed within a solid particle,
b) in the case of a liquid lipid fraction of 50% or more, the disordered liquid lipid being solidified by the solid lipid (solidified oil).

A characteristic of the invention is that disordered and storage-stable structures are produced by adding liquid lipids which lead to partially crystalline or predominantly non-crystalline particles with semi-solid or solid aggregate state.

Solidified oils are known from DE 197 07 309 A1 (Clermont-Gallerande, H., Feste kosmetische Zubereitung auf Basis verfestigter Öle [Solid cosmetic preparation based on solidified oils], 1998). However, these preparations are water-free and do not constitute a dispersion. Instead, this product is used in stick form.

A subsidiary object of the present invention was therefore to provide carrier systems which consist of lipids with physiological tolerability. These carrier systems are intended to have a high loading capacity for active agents and are not intended to change substantially in the course of storage.

It was therefore surprising, and not predictable by the person skilled in the art, that the use of special suspensions, which have liquid oils as substantial constituents, which are amorphously solidified e.g. by waxes, according to claim 1 could achieve this object.

Preferred refinements of this carrier system are in turn the subject matter of the dependent claims.

The term suspension, or dispersion, is used here as a generic term in its widest sense, and describes the distribution of a discontinuous phase in a continuous phase. The discontinuous phase may in this case be semi-solid, partially solid or solid, and is partially crystalline or predominantly non-crystalline. The continuous phase may be liquid, semi-solid or solid, but not gaseous.

The oil phase of the carrier system contains at least two components. The first essential constituent is a liquid oil. The melting point of this oil is below 4° C. Preferred oils are compounds of short-chain (fewer than 14 carbon atoms) fatty alcohols. These include inter alia isopropyl myristate, isopropyl palmitate, isopropyl stearate, octyldodecanol, isopropyl alcohol $C_{6-14}$ dicarboxylates, $C_{14-20}$ branched-chain, aliphatic fatty alcohols, $C_{6-14}$ fatty acid triglycerides and diglycerides, $C_{12-16}$ octanoates, tridecyl salicylates and oils of the Crodamol® group.

The second essential constituent of the oil phase is a lipophilic solidifying substance which is solid at 37° C. This is selected, in particular, from the group consisting of lipids having a melting point above 40° C. and optionally lipophilic gelling agents (e.g. hydrophobic polymers). Suitable substances include esters of long-chain fatty alcohols with long-chain fatty acids, waxes, certain glycerides and long-chain fatty alcohols, in each case having a melting point above 40° C. In particular, this substance is selected from the group consisting of carnauba wax, hydroxyoctacosanyl hydroxystearate, Chinese wax, cetyl palmitate, beeswax and similar waxes. Further examples of these solidifying substances include $C_{20-40}$ di- and triglycerides, including those which contain unsaturated fatty acids, $C_{20-40}$ fatty alcohols, $C_{20-40}$ fatty amines and their compounds, sterols.

The liquid oil and the structuring agent are preferably mixed in a proportion of from 99+1 to 50+50, in particular in a proportion of from 95+5 to 80+20. The mixture of polar oil and structuring agent is, after heating the components together to 90° C. and subsequently cooling to ambient temperature while stirring, semi-solid or solid at 21° C. The mixture is predominantly an amorphous, non-crystalline solid or semi-solid substance. The term solid is here defined as follows, after Bauer et al. (Bauer et al., Pharmazeutische Technologie, $4^{th}$ edition, Georg Thieme Verlag Stuttgart, New York, 1993, page 43):

"Solids are shape-stable bodies which are elastic in response to moderate mechanical forces". Semi-solid substances "are distinguished in that they have only limited shape stability" (Bauer et al., Pharmazeutische Technologie, $4^{th}$ edition, Georg Thieme Verlag Stuttgart, New York, 1993, page 253). The amorphous state is demonstrated by the fact that the mixture has no x-ray reflections, or only very weak or broad ones, in comparison with the crystalline reference substance cetyl palmitate. The absence of crystalline fractions can inter alia be made visible by using a microscope with polarised light. In this case, crystalline regions are in general illuminated whereas amorphous or liquid regions remain dark. The mixture should therefore preferably show no luminous regions through the microscope under polarised light. The crystallinity in the mixture can be measured using dynamic differential scanning calorimetry (DSC). The crystallinity index (CI) can be defined as the ratio between the crystallinity of the raw material and the crystallinity of the mixture of the two components. The crystallinity is in this case determined by the height of the melting peak (e.g. in mW) per gram of the crystalline lipid. The height of the melting peak of the raw material of the solidifying agent is denoted "raw", and the height of the melting peak in the mixture is denoted "mix"

$$CI = \frac{mix}{raw}$$

The crystallinity index is advantageously below 0.5.

The oil phase may contain mixtures of the said components and, besides the said two essential components, further lipophilic substances so that the resulting mixture, after heating the components together to 90° C. and subsequently cooling them to room temperature while stirring, is solid or semi-solid and remains predominantly amorphous. Examples of further components include lipophilic drugs and cosmetic ingredients, plant and natural oils and fats, lipophilic antioxidants, sunscreens, essential oils, perfumes, plant extracts etc.

A third essential constituent of the carrier system according to the invention is water or a liquid which is miscible with water. In a preferred embodiment of the present invention, the water phase contains a gel-forming, structuring additive, which renders the water phase semi-solid and has a yield point of 5 Pa or above at 21° C. (measured e.g. using a rheometer). Suitable structuring additives include hydrophilic polymers, certain inorganic gelling agents and amphiphilic substances. Examples of polymers include alginates, cellulose derivatives, xanthan gum, starch and starch derivatives. Examples of inorganic gelling agents include Aerosil® types and bentonites. Examples of amphiphilic substances having a viscosity-increasing effect include glycerol monostearate and poloxamer 127. Preferred structuring agents are polyelectrolytic polymers such as e.g. polyacrylic acids, carboxymethylcellulose or carrageenan.

The water phase may contain further additives such as e.g. hydrophobic or amphiphilic drugs or cosmetic ingredients, water-soluble antioxidants, preservatives, humectants or plant extracts.

The suspension furthermore contains, as a matter of necessity, substances which increase the physical stability of the suspension. These may be the gel-forming polymers already mentioned above or amphiphilic substances (emulsifying agents). Suitable emulsifying agents include myristyl alcohol, cetyl alcohol, stearyl alcohol, polysorbates, sorbates, block polymers (e.g. poloxamers), glycerol fatty monoacid esters (e.g. glycerol monostearate), esters of polycarboxylic acids and fatty alcohols, or mono- and diglycerides of fatty acids esterified with lactic acid, citric acid or tartaric acid (e.g. glycerol stearate citrate). The use of a combination of at least two emulsifying agents is advantageous. In this case, one emulsifying agent should be charged (positively, negatively or ampholytically). Examples of this include glycerol stearate citrate and quaternary ammonium compounds (cetylpyridinium chloride).

The oil phase, water phase and the suspension stabilisers are mixed in order to obtain intimate distribution of the oil phase in the continuous water phase. The size of the oil droplets is typically between 1 μm and 100 μm. The continuous water phase of the suspension may be characterised e.g. by a fast dissolving capacity for hydrophilic dyes or by miscibility with water. The water phase fraction advantageously constitutes 40-950 of the total suspension.

The lipid particles having a large or predominantly liquid fraction in the lipid mixture (in general >50%) will be explained in more detail with reference to Examples 21 to 26.

The active agent can be released as desired by the transition (crystallisation), induced in a controlled way, into the stable 13 modifications of lipids (Examples 14-16). Stimuli for initiating this transition include adding electrolytes, increasing the temperature or removal of water from the NCC dispersion.

An example of water removal is the drying of particle dispersions after topical application to the skin. In the case of sufficiently sensitive systems, the modification transition and the active-agent release may actually be induced by the electrolytes present on the skin. This is of particular interest for active agents such as cyclosporin (Example 6) which, after topical application, do not penetrate sufficiently into the skin to be able to treat e.g. psoriasis successfully. In contrast to other particulate carriers, in which the release is based on pure diffusion, with NCCs the active agent is released actively from the carrier. The driving force is the induced formation of perfectly crystalline particles, in which there is no longer any space for the active-agent molecules. The drug (e.g. cyclosporin) becomes expelled into the outer phase (e.g. water of the NCC-containing lotion or cream), in which it has low solubility. As a result, the water phase becomes supersaturated with drug and the pressure for the drug's diffusion into the skin is consequently increased (=increase in the thermodynamic activity of the active agent) (FIG. 13). NCCs are therefore suitable, in particular, for active agents with bioavailability problems, e.g. cyclosporins (e.g. cyclosporin A) and structurally related molecules. Mixtures of solid lipids (e.g. Imwitor and Compritol) and liquid lipids (oils (e.g. castor oil, olive oil, maize oil, softigen, isopropyl myristate, octyldodecanol and Miglyols)) have proved to be especially suitable for cyclosporins.

The particles according to the invention may be produced at a high solids concentration as a dispersion. This avoids the above-described disadvantages with the processing of previous low-concentration lipid particle dispersions into other medicinal forms such as e.g. topical dosage forms and cosmetics (creams), oral dosage forms (such as e.g. tablets, pellets and capsules) and in the case of parenterals. Lipid particle dispersions not only can be incorporated into tablets, film tablets and coated tablets, but may also be coated onto them. For this purpose, the tablets or coated tablets are sprayed with the particle dispersion (e.g. in a ball coater (Glatt), Wurster apparatus, fluid-bed drier, Accela Coat) or the lipid particle dispersion is added in a tablet-coating pan. Non-loaded lipid particles may be used to produce a protective film (e.g. against oxygen and humidity), a film for altering the active-agent release or for polishing coated tablets and film tablets. Particles loaded with active agent may provide controlled release of a separate medicament dose, e.g. an initial dose.

Coated tablets and film tablets have hitherto been polished by adding wax balls (e.g. carnauba wax) or by spraying on waxes in organic solvents. The use of lipid particle dispersions (micro- or nanometer particle size) leads to finer distribution of the lipid on the coated-tablet surface in comparison with wax balls (diameter e.g. 1 cm) and avoids organic solvents. Low-concentration lipid particle dispersions cannot be used for this purpose since, because of the high water content, e.g. the coated-tablet surface may partially be dissolved. The particle dispersions according to the invention are, by contrast, distinguished by their relatively low proportion of water.

When producing lipid particles in non-aqueous, preferably oily media and liquid polyethylene glycols (e.g. PEG 400 and PEG 600), soft or hard gelatine capsules may be filled directly with the dispersions. When producing in a PEG which is solid at room temperature (e.g. PEG 6000), the solidified product (dispersion of lipid particles in solid PEG) may be ground, and hard gelatine capsules may be filled with it in powder form.

EXAMPLES

Example 1

Production of a 40% Lipid Particle Dispersion (Solids Content 45%)

The composition of the lipid particle dispersion was 40% cetyl palmitate, 5% saccharose ester S-1670 (Mitsubishi-Kagaku Foods Corporation, Tokyo, Japan) and water to 100%. The lipid was heated to 90° C. and mixed using a rotor-stator stirrer (Ultra-Turrax, Janke & Kunkel, Germany) at 8000 revolutions per minute for two minutes with the hot aqueous solution of the surfactant. The raw emulsion obtained was then homogenised in a Micron LAB 40 at 500 bar and in 3 cycles at 80° C. The product was white and of creamy consistency. After cooling and crystallisation of the lipid nanoparticles, the particle size in the product was measured. The diameter was 246 nm and the polydispersity index was 0.179 (measurement method: photon correlation spectroscopy (PCS), device: Zetasizer 4, Malvern Instruments, UK).

Example 2

Production of a 50% Lipid Particle Dispersion (Solids Content 55%)

The formulation of Example 1 was used, the lipid fraction having been increased from 40% to 50%. Production and homogenisation took place as in Example 1. The product obtained was diluted in order to determine the particle size; the PCS diameter was 325 nm and the polydispersity index was 0.190.

Example 3

Production of a 40% Lipid Particle Dispersion (Solids Content 45%) Using a Rotor-Stator Stirrer Composition of the lipid particle dispersion: 40% fat, 5% saccharose ester S-1670 (Mitsubishi-Kagaku Foods Corporation, Tokyo, Japan) and water to 100%. 24 g of an aqueous surfactant solution was heated to 80° C., and 4 g of molten lipid were added and dispersed for 2 minutes using an Ultra-Turrax (Janke & Kunkel, Germany) at 8000 revolutions per minute. A further 4 g of molten lipid were then added, the dispersion conditions being as before. Successive addition of, in each case, 4 g of molten lipid continued until the total lipid content was 40%. After cooling and crystallisation of the lipid particles, a particle size measurement was carried out in water. The diameter 50% was 12.25 μm (measurement method: laser diffractometry, device: Mastersizer E, Malvern Instruments, UK). A volume distribution curve was measured.

Example 4

Production of a 70% Lipid Particle Dispersion (Solids Content 75%)

The formulation of Example 3 was employed with 5% saccharose ester, but the lipid content was increased from 40% to 70%. Production took place as in Example 3, 4 g of lipid being added successively in each case until the maximum lipid concentration was 70%. After cooling, a diameter 50% of 20.68 μm was measured (laser diffractometry as Example 3).

Example 5

Storage Stability of the Highly Concentrated Lipid Particle Dispersions

The dispersion of Example 1 was stored at room temperature for days. Determining the particle size using PCS gave a diameter of 243 nm and a polydispersity index of 0.203. There was no significant particle size increase, and the dispersion is physically stable in the highly concentrated form.

Example 6

Production of a Drug-Containing 50% Lipid Particle Dispersion (Solids Content 55%)

The composition of the lipid particle dispersion was 48% Imwitor 900, 2% cyclosporin A, 5% Tween 80 and water to 100%. The lipid and medicament were heated to 90° C. and mixed using a rotor-stator stirrer (Ultra-Turrax, Janke & Kunkel, Germany) at 8000 revolutions per minute for 2 minutes with the hot aqueous solution of the surfactant. The raw emulsion obtained was then homogenised in a Micron LAB 40 at 500 bar and in 3 cycles at 80° C.

Example 7

The cyclosporin-loaded lipid particle dispersion was examined with respect to crystalline status using differential scanning calorimetry (DSC). The measurements show that the lipid particles are predominantly in $\alpha$ modification (onset temperature 51.5° C., peak maximum 58.7° C.), whereas the pure lipid has predominantly $\beta$ modification (onset temperature 54.2° C., peak maximum 61.9° C.) (FIG. 5).

Example 8

Production of a 80% Lipid Particle Dispersion (Solids Content 85%)

The formulation of Example 1 was used, the lipid fraction being increased from 40% to 80%. A 50% lipid particle dispersion was first produced in a similar way to Example 1. 10% of lipid was in each case added successively in sub-steps to the product obtained while stirring by means of a rotor-stator stirrer at 8000 revolutions per minute until an 80% lipid particle dispersion was obtained. A diameter 99% of 77.66 µm was measured after cooling (laser diffractometry as Example 3).

Example 9

Atomisation of a 10% Lipid Particle Dispersion by Means of a Pariboy

Paul Ritzau Pari-Werk GmbH, Starnberg, Germany

The composition of the lipid particle dispersion was 10% cetyl palmiate, 1.2% Tego Care 450 and water to 100%. Production and homogenisation took place as in Example 1. The product obtained was atomised by means of a Pariboy and the resulting aerosol was collected in a beaker. The diameter 50% was 0.28 µm before and 0.30 µm after atomisation (laser diffractometry as Example 3).

Example 10

Production of Liquid/Solid Particles Using Imwitor

The composition was 10% Imwitor, 5% Miglyol 812, 0.5% retinol, 2.5% Miranol (sodium cocoamphoacetate) and 82% water. The lipids Imwitor and Miglyol were mixed in the molten state at 90° C. and then particles were produced as in Example 1. The PCS diameter was 188 nm and the polydispersity index was 0.266. The wide-angle x-ray diffractogram (FIG. 5, left) confirms the predominant presence of the fat in the liquid state ($\alpha$ modification).

Example 11

Production of Liquid/Solid Particles Using Compritol

Production took place as in Example 10, the lipid Imwitor having been replaced by Compritol. The Miranol concentration was here 1.5%. The PCS diameter was 225 nm and the polydispersity index was 0.205.

Example 12

Production of Liquid/Solid Particles with Different Proportions of Liquid Lipid

Compritol particles were produced as described in Example 11. The lipid fraction was constant at 15% (solid lipid Compritol oil Miglyol) in the aqueous dispersion, the proportion of oil to solid lipid having been changed. Particles were produced with 8.3%, 16.7%, 28% and 38% oil fraction in the lipid (i.e. 91.7%, 83.3%, 72% and 62% Compritol). At a low oil fraction (8.3%) in the mixture, the oil dissolves predominantly in the solid lipid (molecularly disperse distribution) and only a few nano-compartments of liquid oil result. Oil distributed in a molecularly disperse form cannot crystallise; crystallisation and release of crystal lattice energy occur only when there is a sufficiently great accumulation of molecules (e.g. nano-compartment), so the measured enthalpy of melting, calculated in terms of the total amount of oil incorporated, is far below the theoretical value of 12 J/g and close to zero (FIG. 6, left). When the oil fraction is increased, the take-up capacity threshold of the solid lipid matrix for oil molecules is reached, and predominantly small regions with liquid oil are formed. These nano-compartments can crystallise and the enthalpy increases linearly from a 16.7% to 38% oil fraction (FIG. 6).

The x-ray diffractograms of the particles confirm that, besides the liquid lipid in $\alpha$ modification detected by DSC, there is also solid lipid in the unstable $\beta'$ modi-fication (peaks at 0.38 nm and 0.42 nm spacing, FIG. 7).

Example 13

Conservation of the Lipid Fraction in Lipid Particles by Inhibiting the Transformation of the Lipid into the Stable $\beta$ Modification 20 parts of aqueous SLN dispersion from Example 10 were incorporated by stirring, into 80 parts of a cosmetic O/W cream (Nivea Visage, Beiersdorf, Hamburg, Germany). After 168 days of storage at room temperature, the x-ray diffractogram showed no change in comparison with the day after production (FIG. 5).

Example 14

Controlled Crystallisation of the Lipid Fraction and Transformation of $\alpha/\beta'$ into the Stable $\beta i/\beta$ Modification by Electrolytes 10 parts of glycerol and 70 parts of water were added to 20 parts of the Imwitor particles from Example 10. 0.4% of Carbopol 940 (polyacrylic acid) are added to this mixture as a gelling agent and 0.1% of sodium hydroxide was then added as an electrolyte. Immediately after production, the liquid/solid lipid particles, still unchanged, show a pronounced liquid fraction of $\alpha$ modification (FIG. 8, left) which becomes a solid lipid particle of the stable $\beta i/\beta$ modification under the influence of the electrolyte (FIG. 8, right).

Example 15

Controlled Transformation of $\alpha/\beta'$ into the Stable $\beta i/\beta$ Modification by Water Removal A Compritol particle dispersion was produced as in Example 11, the Miglyol containing 10% retinol. In order to investigate the release, 200 µl of aqueous SLN dispersion were introduced into a continuous flow Franz cell (Crown Scientific, US-Sommerville) (acceptor medium: isotonic phosphate buffer pH 7.4, flow rate medium: 1.0 ml/h, temperature: 37° C., membrane: cellulose nitrate filter impregnated with isopropyl myristate). The x-ray diffractograms show that the dilution by water leads to formation of a solid lipid particle with stable βi modification (FIG. 9, peak at 0.46 nm spacing). As the transition into a solid particle with fewer crystal defects progresses, increasingly more drug is expelled from the particle, that is to say the release (drug flux) increases with time (=increasing degree of crystallisation) (FIG. 10). For comparison, a nanoemulsion with a comparable drop size was produced by replacing Compritol with Miglyol in the production process (PCS diameter: 186 nm, PI 0.113).

Example 16

Retinol-loaded particles were produced as in Example 15. 10 parts of glycerol and 70 parts of water were added to 20 parts of the particle dispersion. 0.5% of xanthan gum was added to this mixture. The hydrogel formed was investigated in the Franz cell as in Example 15. As a result of the water dilution, the more stable βi modification also formed in the hydrogel (FIG. 11), the drug was expelled from the lipid matrix to an increasing extent and the flux (drug release) increased with time (FIG. 12).

Example 17

Production of a Dispersion for Polishing Coated Pills

Lipid particles based on carnauba wax were produced by high pressure homogenisation (31% carnauba wax, 3% surfactant, water). Production was carried out using a Micron LAB 40 at 95° C., 500 bar and 3 cycles. The PCS diameter was 420 nm and the polydispersity index was 0.185.

Example 18

Prolonged Active-Agent Release of Citrus Oil from Stearic Acid Particles in Comparison with Miglyol Emulsions A lipid particle dispersion consisting of 10% (m/m) stearic acid, 1% (m/m) citrus oil, 1.2% (m/m) Tween® 80 and water was produced by high-pressure homogenisation. The mixture of lipid and emulsifying agent was melted at 75° C. and dispersed in the aqueous solution using an Ultra-Turrax T25 with dispersing tool S25, Janke & Kunkel (8000 rpm, for 1 minute). The raw emulsion obtained was then homogenised using an APV Gaulin LAB 40 homogeniser at 500 bar in 3 cycles at 75° C. Lipid particles having a mediam LD diameter (LD d50%) of 215 nm resulted. As a comparison, an emulsion system was similarly produced, the 10% stearic acid having been replaced by 10% Miglyol 812. The LD d50% was here 195 nm. In vitro release experiments at 32° C., which were evaluated using UV spectrophotometry, confirmed prolonged release from the SLN dispersion (no burst release as in the case of the emulsion). After 6 hours, the cumulative release from the SLN dispersion was reduced by 50% in comparison with the emulsion. (FIG. 14).

Example 19

Prolonged Active-Agent Release of the Perfume Oil Allure (Chanel) from Stearic Acid Particles in Comparison with Miglyol Emulsions A lipid particle dispersion consisting of 10% (m/m) stearic acid, 1% (m/m) Allure, 1.2% (m/m) Tween® 80, and water was produced by high-pressure homogenisation in a similar way to Example 18. Lipid particles having an average PCS diameter of 336 nm and a polydispersity index 0.137 resulted. As a comparison, an emulsion system was similarly produced, the 10% stearic acid having been replaced by 10% Miglyol 812. In vitro release experiments at 32° C., which were evaluated using UV spectrophotometry, confirmed prolonged release from the SLN dispersion. After 6 hours, 100% of the perfume oil had already been released from the emulsion system; the release from the SLN dispersion was, however, only 75% at this time.

Example 20

Lipid particle dispersions were produced with Witepsol H15 ($C_{12}$-$C_{18}$ hard fat) and Witepsol E85 ($C_{12}$-$C_{18}$ hard fat) by high-pressure homogenisation (three cycles, 500 bar, production temperature 85° C., device LAB 40). The particle sizes were 119 nm and 133 nm (PCS diameter). The lipid particles were examined with respect to the change in the relaxation times T1 and T2 using a Bruker mini-spec pc 120. The relaxation times were T1=0.1498 s and T2=0.0707 s (Witepsol E85) and T1=0.1577 s and T2=0.1191 s (Witepsol H15).

Example 21

This example shows in 1 the composition of a typical suspension, which complies with the claims of this invention. As a comparative example, the formulation V1 is indicated which does not comply with the claims of this invention.

|  | 1 | V1 |
|---|---|---|
| Vaseline | — | 5.0% |
| Paraffin oil | — | 10.0% |
| Dimeticon 100 | — | 5.0% |
| Jojoba oil | — | 4.0% |
| Isopropyl myristate | 10.0% | — |
| Medium chain triglycerides | 10.0% | — |
| Hydroxyoctacosanyl hydroxystearate | 4.0% | — |
| Retinaldehyde | 0.2% | 0.2% |
| Glycerol monostearate | 0.3% | 0.3% |
| Cetyl alcohol | 0.5% | 0.5% |
| Polysorbate 80 | 0.5% | 0.5% |
| Glycerol stearate citrate | 2.0% | 2.0% |
| Sorbitol | 5.0% | 5.0% |
| Polyacrylic acid | 0.5% | 0.5% |
| Sodium hydroxide | to adjust the pH (pH 6-7) | to adjust the pH (pH 6-7) |
| Sodium chloride | 0.5% | 0.5% |
| Water | to 100% | to 100% |

The lipophilic components, including the active agent, and the hydrophilic components, including the emulsifying agent but without the polyacrylic acid, are heated separately to 90° C. and mixed at 90° C. The mixture is dispersed at this temperature for five minutes using an Ultra-Turrax at 10,000 revolutions per minute. After cooling to 40° while stirring, the polyacrylic acid was added, dispersed for a further 1 minute using the Ultra-Turrax and the suspension is subsequently cooled to ambient temperature while stirring.

Example 22

This example demonstrates the possibility of stabilising unstable active agents by means of the invention. The comparative formulation V1 shows no amorphously solidified oil phase and does not therefore have a composition according to the invention. The stabilities of the two retinaldehyde-containing preparations from Example 21 are listed in Table 1. Storage takes place at room temperature (RT) or 40° C. in closed glass vessels which contain ⅓ the preparation and ⅔ air. The values are expressed in percent of the starting concentration. The contents were determined using UV spectroscopy at a detection wavelength of 325 nm.

TABLE 1

| Time (d) | 14 days | | 28 days | | 84 days | |
| --- | --- | --- | --- | --- | --- | --- |
| | RT | 40° C. | RT | 40° C. | RT | 40° C. |
| 1 | 92.6 | 75.1 | 89.2 | 64.2 | 82.8 | 35.7 |
| V1 | 85.9 | 62.8 | 76.7 | 35.2 | 60.1 | 9.0 |

Table 1 clearly shows that, after 12 weeks of storage at 40° C. for the carrier system according to the invention, a many times higher amount of the active agent was found that in a comparison emulsion.

Example 23

This example demonstrates the possibility of reducing the irritant effect of incorporated active agents. The active agent used, benzyl nicotinate, causes hyperaemia of the skin, which can be identified by reddening of the relevant skin areas. 8 mg of the preparations 2 and V2 were respectively distributed uniformly without pressure on two skin areas of size 2 cm×2 cm. The reddening of the two areas was compared at specific time intervals and assessed on a scale of from 0 (no skin reddening) to 4 (very strong skin reddening). The preparations 2 and V2 had the following compositions:

| | 2 | V2 |
| --- | --- | --- |
| Isopropyl myristate | 10.0% | 10.0% |
| Medium chain triglycerides | 10.0% | 10.0% |
| Hydroxyoctacosanyl hydroxystearate | 5.0% | — |
| Jojoba oil | — | 5.0% |
| Benzyl nicotinate | 2.5% | 2.5% |
| Glycerol monostearate | 0.3% | 0.3% |
| Cetyl alcohol | 0.5% | 0.5% |
| Polysorbate 80 | 0.5% | 0.5% |
| Glycerol stearate citrate | 2.0% | 2.0% |
| Sorbitol | 5.0% | 5.0% |
| Polyacrylic acid | 0.8% | 0.8% |
| Sodium hydroxide | to adjust the pH (pH 7-8) | to adjust the pH (pH 7-8) |
| Sodium chloride | 0.5% | 0.5% |
| Water | to 100% | to 100% |

Preparation 2 has a composition according to the invention, and possesses a solidified oil phase, so that the active agent is immobilised better. Preparation V2 does not have a composition according to the invention. The solid wax hydroxyoctacosanyl hydroxystearate of preparation 2 was replaced in V2 by the liquid wax jojoba oil, so that the oil phase remains completely liquid and the active agent cannot consequently be immobilised.

The profile of the skin reddening as a function of time is represented in FIG. 15. The arithmetic means of 4 people (2 male, 2 female, in each case left forearm, no skin diseases) are plotted. FIG. 15 shows that in the case of the emulsion 2 according to the invention (solid line) the reddening sets in slower and the peak of the profile is smoothed in comparison with V2 (broken line). This implies a reduction in the irritant effect of the active agent by its incorporation into the carrier system.

Example 24

This example demonstrates a possible method of detecting the solid nature of the oil droplets in the suspension. The mixture of solidifying wax and liquid oil must, as described above, be an amorphous solid or semi-solid substance. The shape stability, as defined above, can be demonstrated macroscopically in the coarse mixture. A possible method which can detect the solid nature of the oil droplets, some of which are only a few micrometers in size, in the suspension will be described below. It involves proton resonance spectroscopy ($^1$H-NMR). This can measure the mobility of the fat molecules. Very mobile molecules lead to very intense and sharp resonance signals. Very immobile molecules, on the other hand, produce resonance signals only of weak intensity and large signal width (Rücker et al., Instrumentelle pharmazeutische Analytik [Instrumentational pharmaceutical analysis], $2^{nd}$ edition, Wissenschaftliche Verlagsgesellschaft mbH Stuttgart, page 172, 1992). In this method, the carrier system according to the invention is compared with an emulsion not according to the invention (reference emulsion), in which the solidifying substance is replaced by a corresponding amount of the liquid wax jojoba oil. The signals used for evaluation are those between 0.8 and 2.6 ppm, which correspond to the signals of the protons of the fatty acid chains, in particular the strongest signal at approximately 1.25 ppm. The intensity is the height of these signals and the linewidth is the width measured at half the height of the signal. The suspension according to the invention shows the less intense and broader signals compared with the reference formulation. The solidification of the oil droplets is shown in particular by:
  the linewidth of a proton signal of the carrier system is at least twice as wide as the linewidth of the corresponding signal of the reference emulsion and/or
  the intensity of a signal of the carrier system is at most half the intensity of the corresponding signal of the reference emulsion.

FIG. 16 represents the $^1$H-NMR spectra of suspension 2 (upper spectrum) and of the comparison formulation V2 (lower spectrum) from Example 23. For suspension 2, the intensity of the signal at 1.22 ppm is 2.48 units and the linewidth is 0.058 ppm. The reference formulation V2 has an intensity of 5.82 units and a linewidth of 0.037 ppm for the signal at 1.22 ppm.

The solidifying substance can build a network in the oil droplets and hence create the shape stability. The solidifying substance can also be distributed diffusely in the matrix of the liquid oil and hence create the shape stability.

Example 25

This example illustrates the above-defined crystallinity index (CI). The raw material is measured first. The height of the melting peak of e.g. hydroxyoctacosanyl hydroxystearate at 76.5° C. is 1245.9 mW per gram of hydroxyoctacosanyl hydroxystearate (measured using a differential heat flux calorimeter). Secondly, 70 parts of the oil consisting of medium chain triglycerides (Miglyol 812) is mixed with 30 parts of hydroxyoctacosanyl hydroxystearate, this mixture is heated to 90° C. and allowed to cool while stirring. Measurement using a differential heat flux calorimeter now gives a height of the melting peak at 68.9° C. of 310.6 mW per gram of hydroxyoctacosanyl hydroxystearate. The CI is therefore calculated as:

$$CI = \frac{310.6 \text{ mW}}{1245.9 \text{ mW}} = 0.25$$

The crystallinity of the raw substance is therefore drastically reduced in the mixture. The oil phase is predominantly non-crystalline.

Example 26

X-ray diffractometry can be employed to demonstrate the amorphous nature of the solidified oil droplets. FIG. 17 shows x-ray diffractograms for a 2 theta angle range=18-26°. FIG. 17 shows at the top (1) the diffractogram of the formulation V2 from Example 23, in the middle (2) the formulation 2 from Example 23 and at the bottom a corresponding amount of crystalline cetyl palmitate. The formulation V2 is, as expected, predominantly x-ray amorphous (liquid oil droplets) (1). The formulation 2 is likewise x-ray amorphous, in spite of the hydroxyoctacosanyl hydroxystearate present in the solid form, and therefore meets the requirements of this invention (2). Crystalline cetyl palmitate, on the other hand, shows two intense reflections and is therefore not amorphous (3). A definition of predominantly amorphous which may in particular be used in the sense of this invention is that the intensity (height) of a reflection of the suspension amounts to at most 50% of the intensity of the reflection of the corresponding solid raw material, in each case expressed in terms of the same amount by weight of the raw material.

Figure 1:
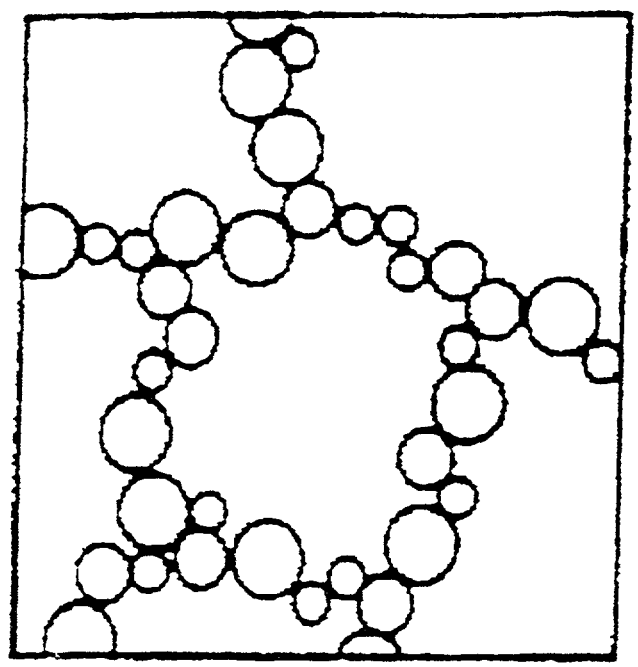
FIG. 1: structure of a gel framework of spherical Aerosil (silicon dioxide) particles.
Figure 2:
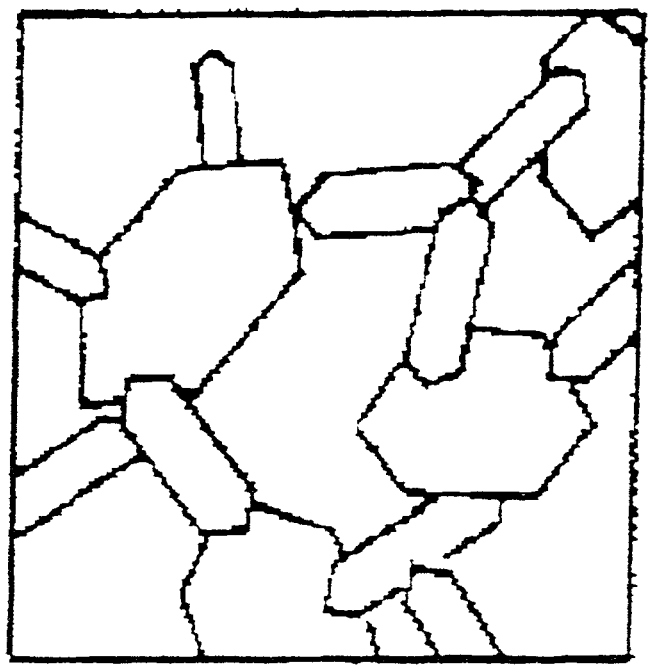
FIG. 2: structure of a polydisperse gel framework of magnesium-aluminium silicate (bentonite).
Figure 3:
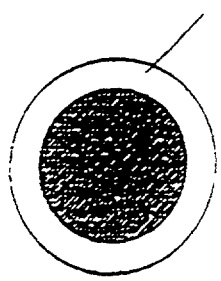
FIG. 3: formation of solid bridges upon contact of lipid particles by solidification of the outer shell.
Figure 3:
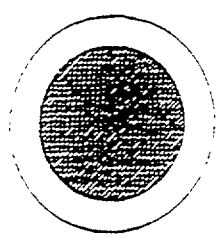
Figure 3:
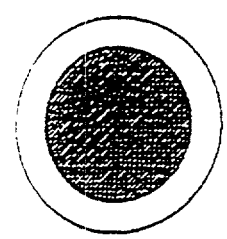
Figure 3:
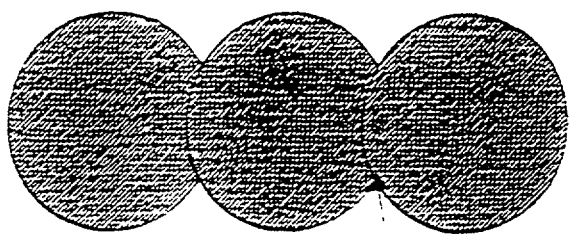
Figure 4:
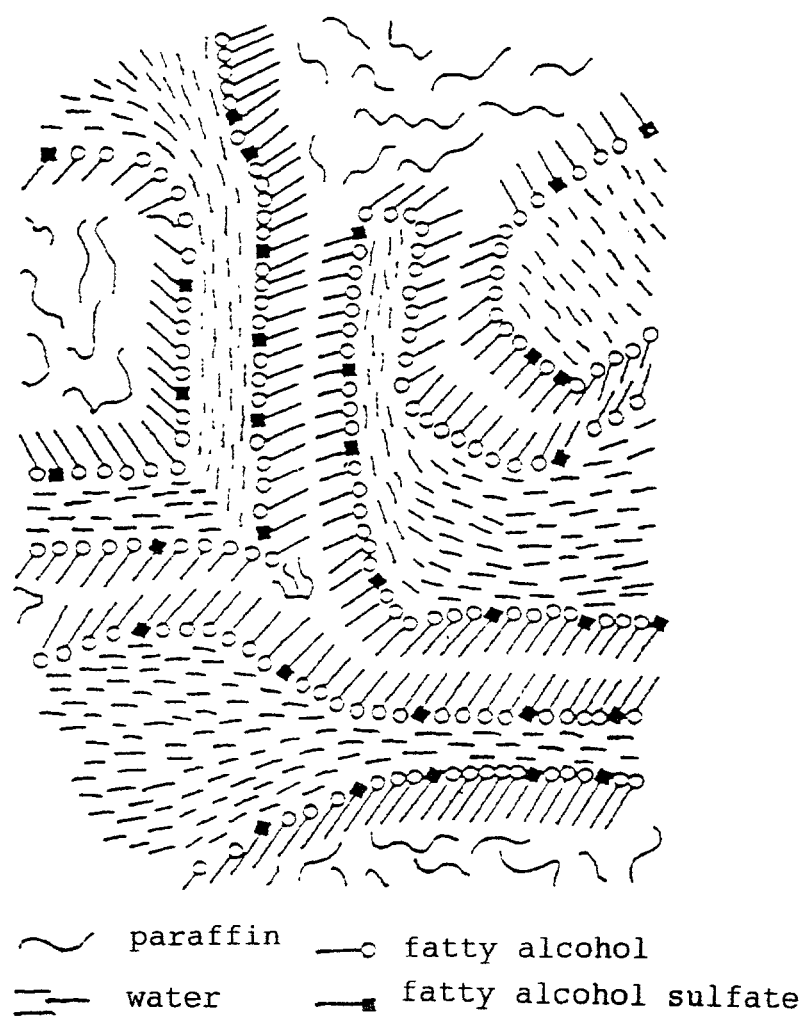
FIG. 4: structure of a biamphiphilic cream.
Figure 5:
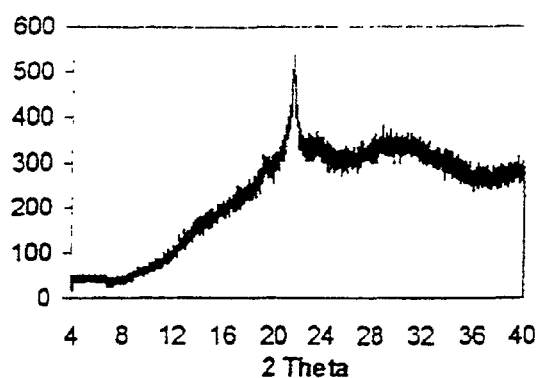
FIG. 5: x-ray diffractograms of the Imwitor particle dispersion in creams (Examples 10 and 13) on the day after production (left) and after 168 days of storage (right).
Figure 5:
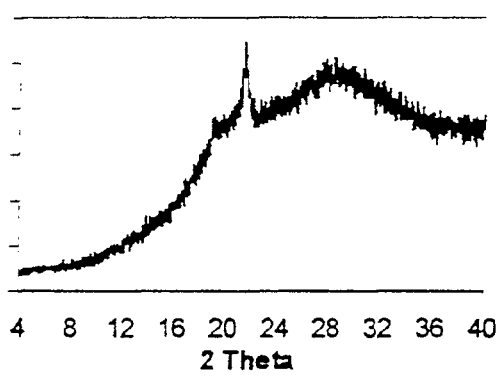
Figure 6:
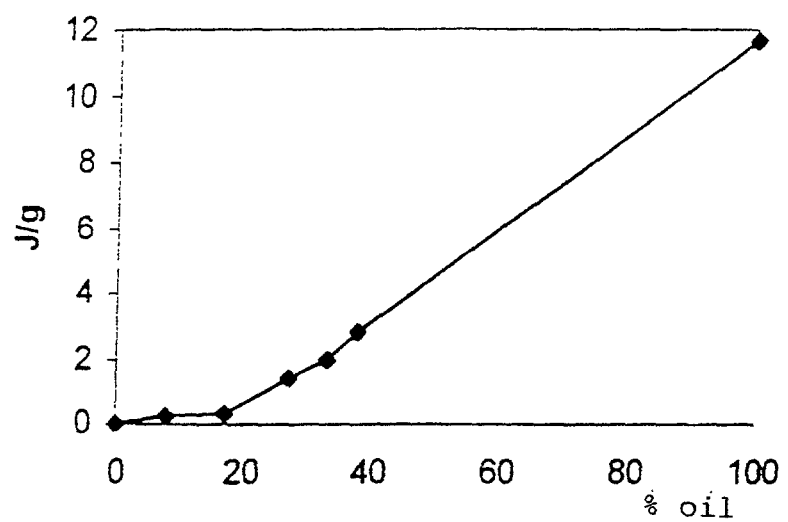
FIG. 6: heat of crystallisation (J/g) of the liquid lipid in the particles from Example 12 as a function of the oil content in the lipid mixture consisting of liquid Miglyol and solid Compritol. Comparison: emulsion produced by using Miglyol, i.e. lipid consists of 100% oil. (Analysis using DSC (differential scanning calorimetry), temperature range: −20 to −60° C., cooling rate: 5 K/min, Mettler Toledo DSC 821e, Mettler, Giegen).
Figure 7:
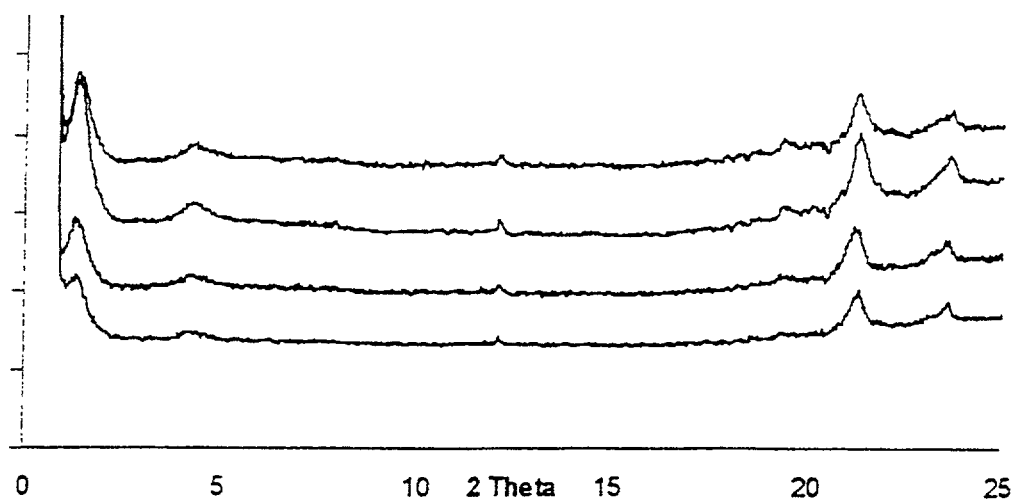
FIG. 7: x-ray diffractogram of the particles with increasing oil fraction from Example 12. From top to bottom: oil fraction in the lipid: 38%, 28%, 16.7% and 8.3%.
Figure 8:
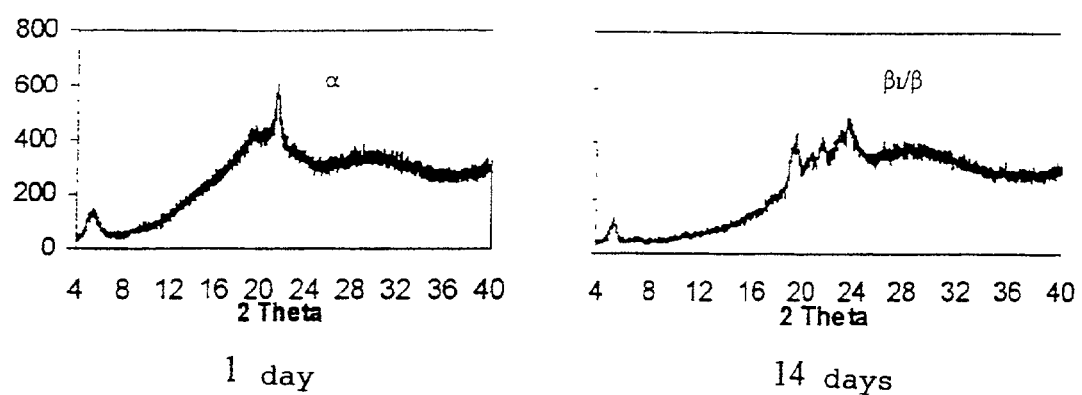
FIG. 8: x-ray diffractograms of the Imwitor particle dispersion immediately after incorporation into a Carbopol gel and after transformation into a solid particle by electrolyte addition (Example 13).
Figure 9:
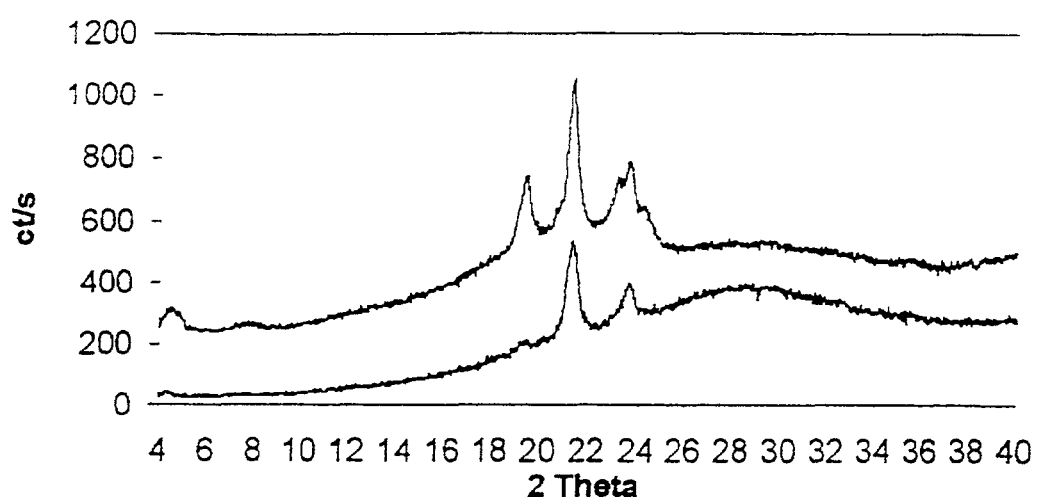
FIG. 9: x-ray diffractogram of the particle dispersion from Example 14 before introduction into the Franz cell (curve at the bottom) and after water evaporation over the measurement period of 24 hours (top).
Figure 10:
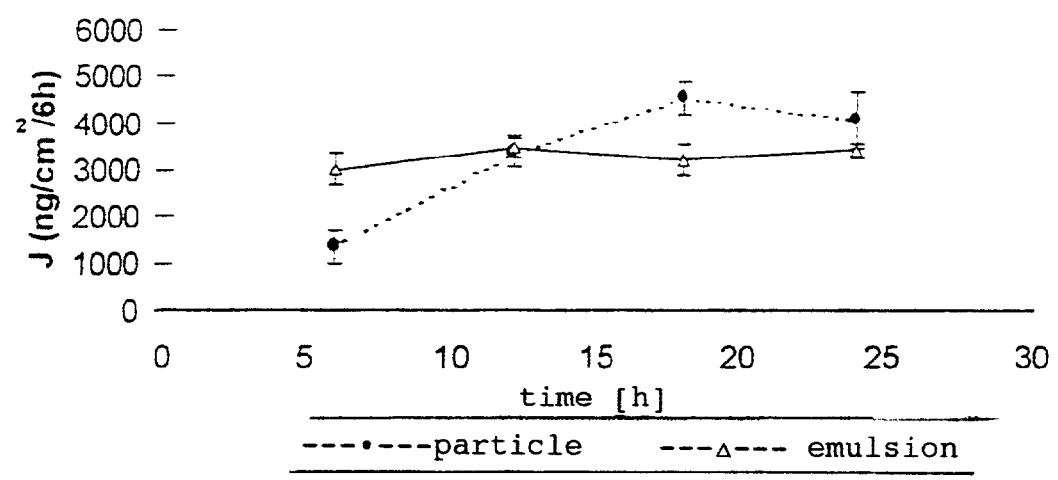
FIG. 10: increasing retinol flux from the dispersion with liquid/solid particles from Example 14 in the course of the transformation to the solid particle in βi modification. For comparison: constant release of retinol from liquid particles (oil droplets of an emulsion).
Figure 11:
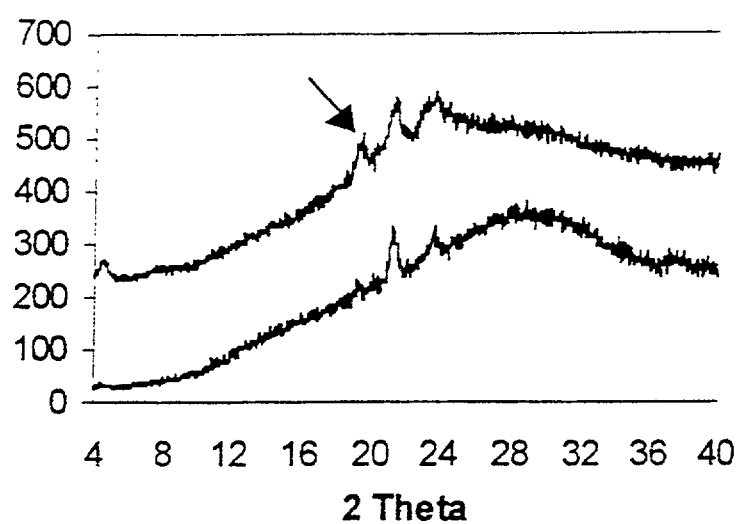
FIG. 11: x-ray diffractogram of the hydrogel of Example 15 containing liquid/solid lipid particles before introduction into the Franz cell (curve at the bottom) and after water evaporation over the measurement period of 24 hours (top, arrow: peak for βi modification).
Figure 12:
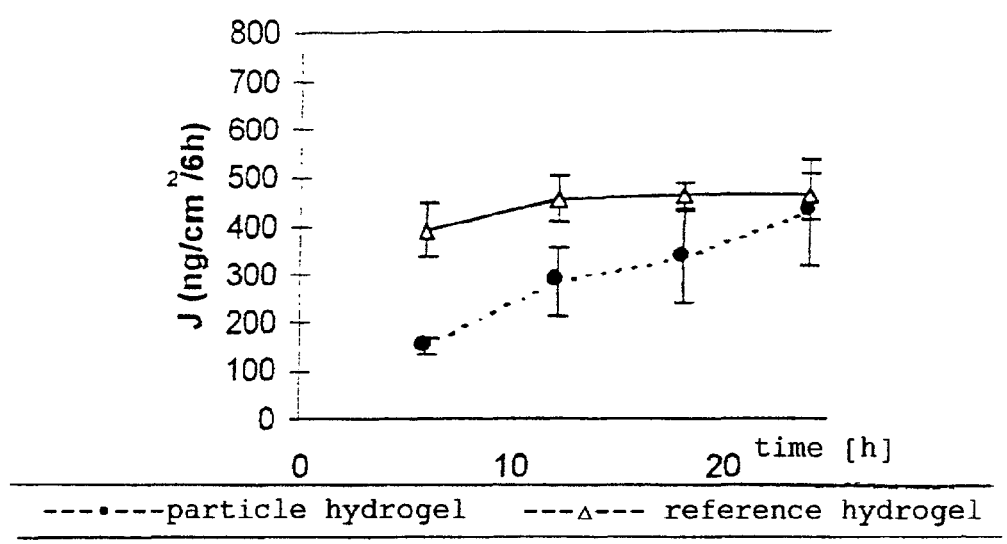
FIG. 12: increasing retinol flux from the hydrogel of Example 15 containing liquid/solid lipid particles in the course of the transformation to the solid particle in βi modification. For comparison: constant release of retinol from liquid particles (oil droplets of an emulsion) in an identical hydrogel base.
Figure 13:
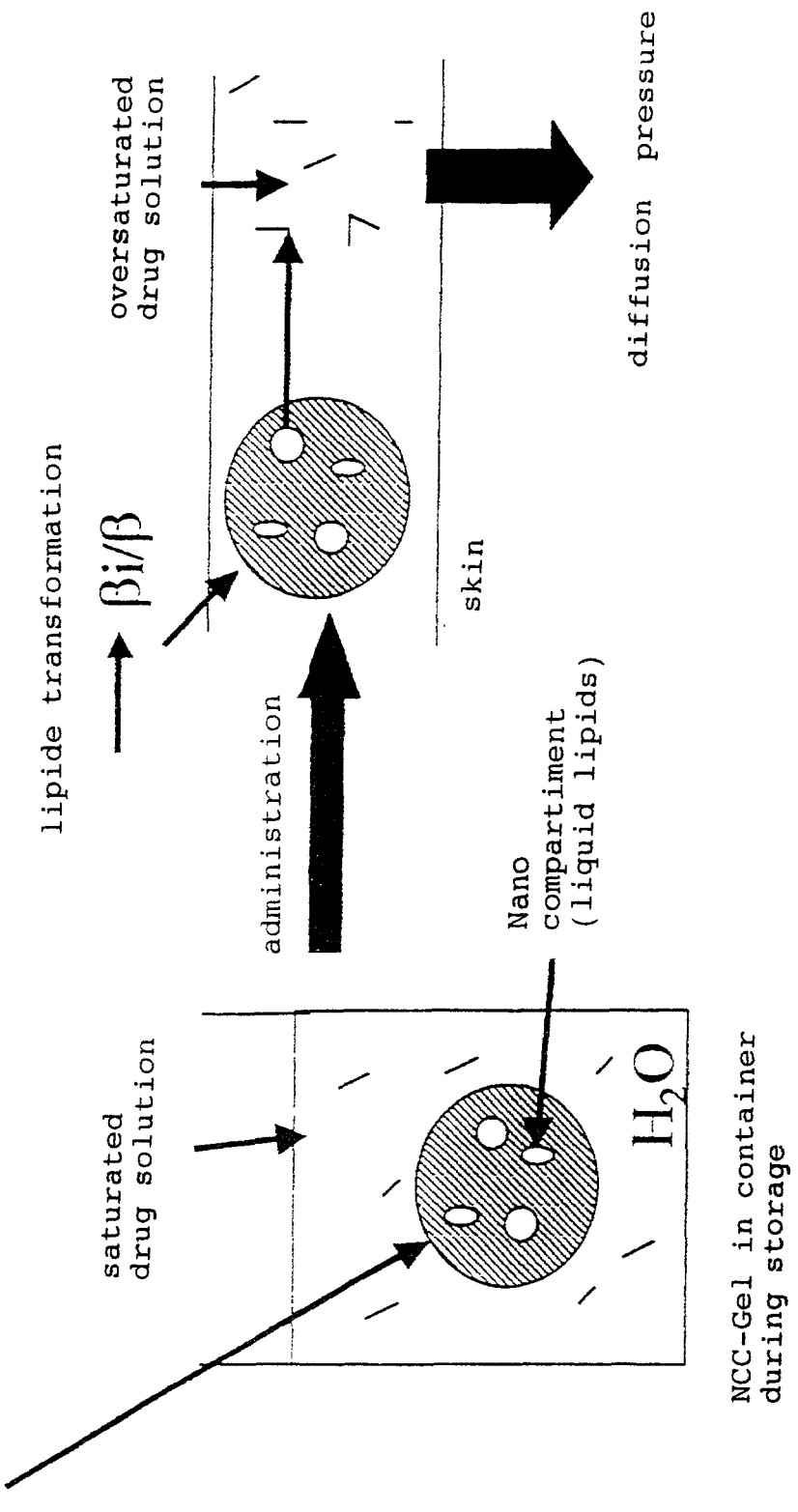
FIG. 13: model for the active-agent release from cyclosporin/lipid particles (Example 6).
Figure 14:
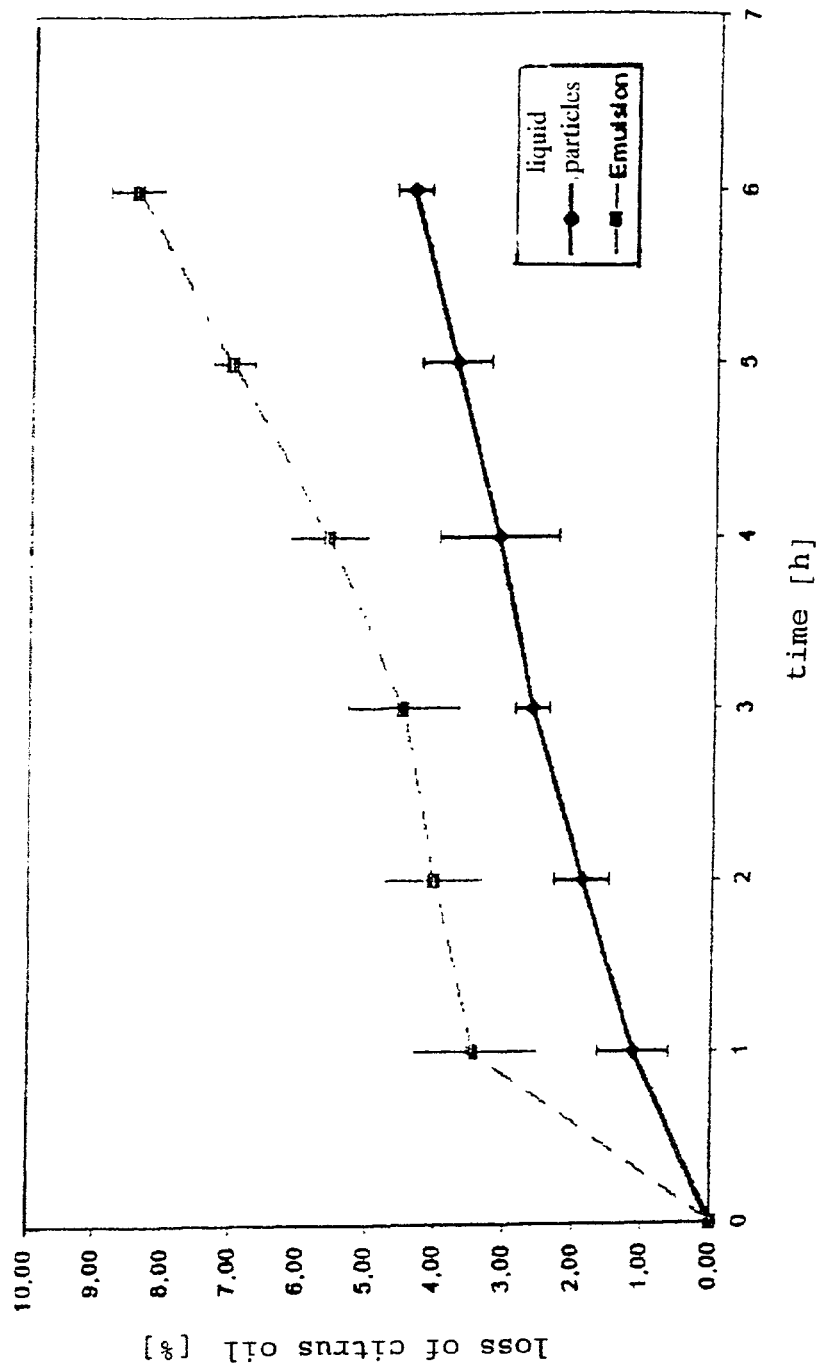
FIG. 14: release of citrus oil at 32° C. from the SLN dispersion and the emulsion.
Figure 15:
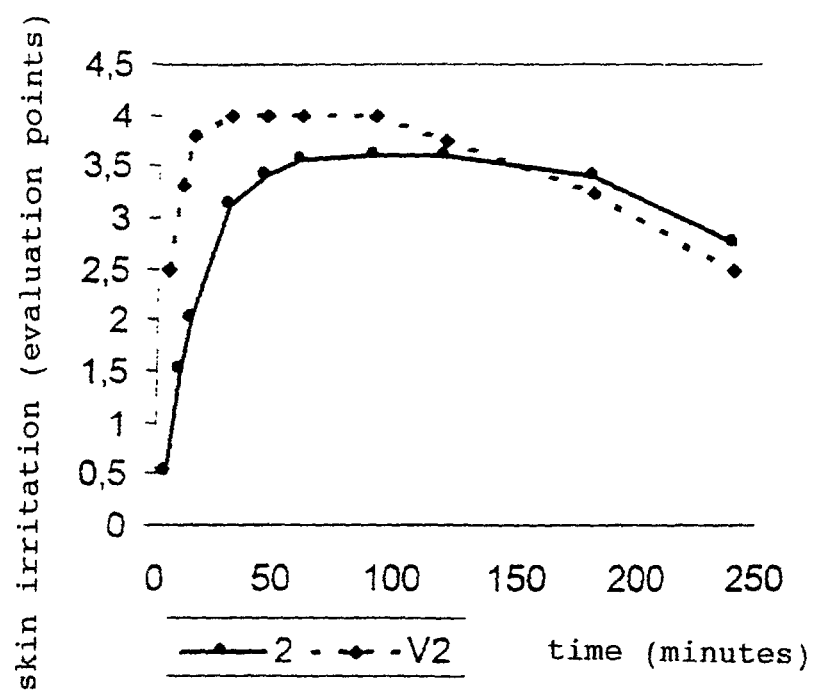
FIG. 15: reduction in the irritant effect of the active agent by its incorporation into the carrier system.
Figure 16:
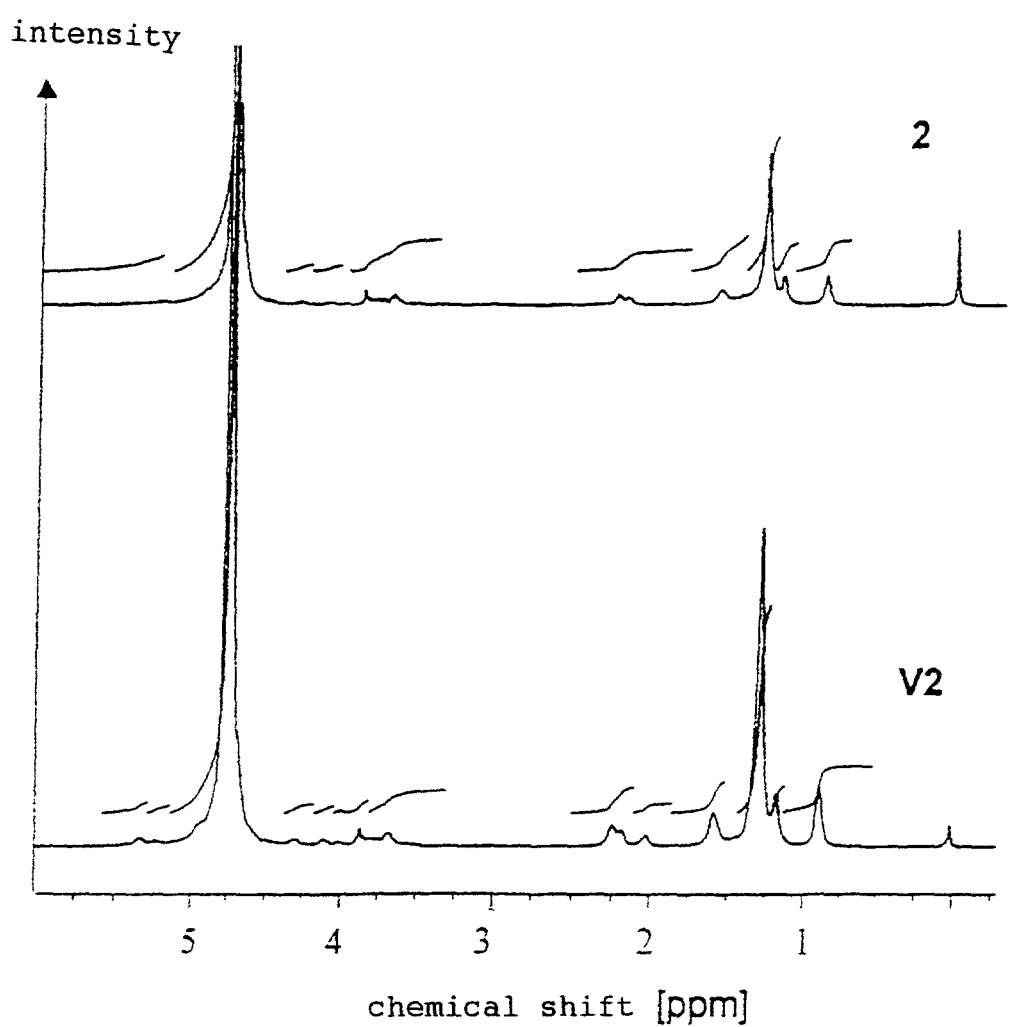
FIG. 16: $^1$H-NMR spectra of suspension 2 (upper spectrum) and of the reference formulation V2 (lower spectrum) from Example 23.
Figure 17:
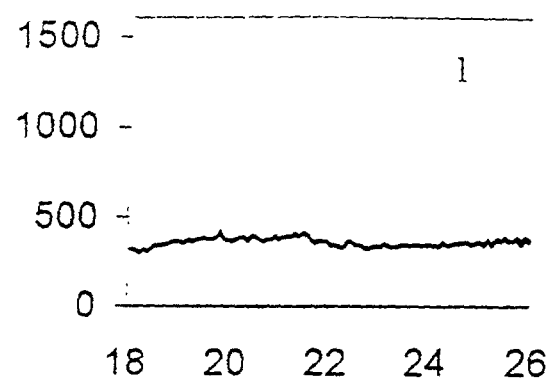
FIG. 17: x-ray diffractograms for a 2 theta angle range 18-26°; top (1) the diffractogram of the formulation V2 from Example 23, in the middle (2) the formulation 2 from Example 23 and at the bottom a corresponding amount of crystalline cetyl palmitate.
Figure 17:
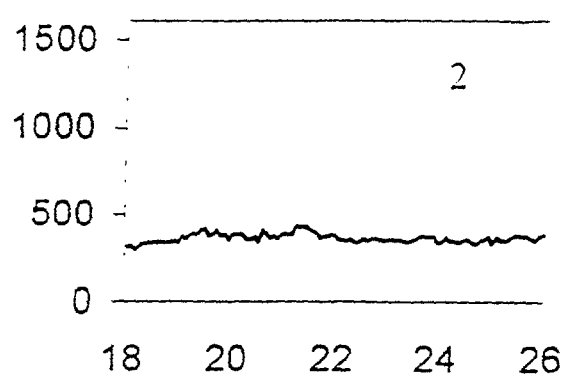
Figure 17:

The invention claimed is:

1. An Ointment or lotion for topical application comprising lipid particles comprising a matrix prepared from a blend of
   a) a lipid which is solid at 37° C. (solid lipid) or a mixture of such solid lipids, and
   b) a lipid which has a melting point below 4° C. (liquid lipid) or mixtures of such liquid lipids, wherein, at 20° C., the particles are definite particles possessing a particle matrix structure which is not completely in the polymorphic, stable β-modification, the particle matrix comprises a predominant fraction of liquid lipid or lipid in the liquid crystalline state (α-modification), such that the particle matrix is less ordered compared to the bulk material of the initial solid lipid, the crystallinity index being below the crystallinity index of the initial solid lipid is below 0.5, and the average particle size being in the nanometer range of 30 to 1000 nm (0.03 to 1.0 μm), wherein the liquid lipid, or a mixture of liquid lipids, and the solid lipid, or a mixture of solid lipids, are mixed in a proportion of from 80+20 to 0.1+99.9.

2. The ointment or lotion according to claim 1, wherein, at 21° C., the lipid particles consisting of a mixture of liquid lipid and solid lipid are predominantly x-ray amorphous and predominantly non-crystalline, and therefore have a high degree of disorder (non-crystallinity), the aggregate state of the particles being partially solid, semi-solid or solid.

3. The ointment or lotion according to claim 2, wherein the liquid lipid, or a mixture of liquid lipids, and the solidifying solid lipid, or a mixture of solid lipids, are mixed in a proportion of from 50+50 to 99+1.

4. The ointment or lotion according to claim 1, wherein the lipid particles are dispersed (suspension) in an outer phase (dispersion medium) and the suspension comprises:
   a) one or more oils which are liquid at 4° C.,
   b) one or more lipophilic substances which at 37° C. are solid and solidify the liquid oil,
   c) a water phase or water-miscible phase, d) one or more substances for increasing the physical stability of the suspension, e) one or more active agents, which are predominantly contained in the lipid droplets, f) optionally natural antioxidants and synergists of the natural antioxidants, g) optionally further cosmetic or pharmaceutical active agents and excipients.

5. The ointment or lotion according to claim 1, wherein the lipid particles contain one or more active agents.

6. The ointment or lotion according to claim 5, wherein the active agents in the active agent-containing lipid particles are lipophilic, are hydrophilic, or are insoluble in the suspension.

7. The ointment or lotion according to claim 1, wherein the particles are produced from the following individual lipids or their mixtures: natural or synthetic triglycerides or mixtures thereof, monoglycerides and diglycerides, alone or mixtures thereof or with triglycerides, self-emulsifying modified lipids, natural and synthetic waxes, fatty alcohols, including their esters and ethers and in the form of lipid peptides, apolipoproteins or any mixtures thereof.

8. The ointment or lotion according to claim 7, wherein the lipids comprise synthetic monoglycerides, diglycerides and triglycerides as individual substances or as a mixture, Imwitor 900, triglycerides, waxes, in particular cetyl palmitate, carnauba wax or white wax (DAB) and/or hydrocarbons.

9. Ointment or lotion for topical application comprising Lipid particle dispersions comprising lipid particles dispersed in an outer phase (dispersion medium), wherein in each case expressed in terms of the weight of the dispersions, they have a content of lipid particles of from 30% to 95% or a solids content of from 30% to 95% (lipid and stabiliser), wherein the lipid particles comprise a matrix prepared from a blend of a) a lipid which is solid at 37° C. (solid lipid) or a mixture of such solid lipids, and b) a lipid which has a melting point below 4° C. (liquid lipid) or mixtures of such liquid lipids, and wherein, at 20° C., the particles are definite particles possessing a particle matrix structure which is not completely in the polymorphic, stable β-modification, the particle matrix comprises a predominant fraction of liquid lipid or lipid in the liquid crystalline state (α-modification), such that the particle matrix is less ordered compared to the bulk material of the initial solid lipid, the crystallinity index being below the crystallinity index of the initial solid lipid is below 0.5, and the average particle size being in the nanometer range of 30 to 1000 nm (0.03 to 1.0 μm), wherein the liquid lipid, or a mixture of liquid lipids, and the solid lipid, or a mixture of solid lipids, are mixed in a proportion of from 80+20 to 0.1+99.9.

10. The ointment or lotion according to claim 9, wherein the outer phase (the dispersion medium) is water, is non-aqueous, is an oily or organic liquid or comprises mixtures thereof.

11. The ointment or lotion Lipid particle dispersions according to claim 10, wherein the outer phase (the dispersion medium) is non-aqueous.

12. The ointment or lotion according to claim 10, wherein characterised in that the outer phase is an oily or organic liquid.

13. The ointment or lotion according to claim 9, wherein the particles are stabilised in dispersion by surfactants, stabilisers, polymers, charged stabilisers, and/or anti-flocculants individually or in their mixture.

14. The ointment or lotion according to claim 13, wherein the steric stabilisers and/or polymers comprise poloxamers and poloxamines.

15. The ointment or lotion according to claim 13, wherein the surfactants comprise alkali metal soaps, metal soaps, amine soaps, alkyl sulphates, alkyl sulphonates, fatty alcohols, or fatty acids, fatty acid sorbates, esters and ethers of sugars or sugar alcohols with fatty acids or fatty alcohols and/or natural surfactants.

16. The ointment or lotion according to claim 13, wherein the charged ionic stabilisers comprise diacetyl phosphates, phosphatidyl glycerol, lecithins, chemically modified lecithins, sphingolipids, sterols, saturated and unsaturated fatty acids, bile acid salts, sodium cholate, sodium glycocholate, sodium taurocholate, sodium deoxycholate or their mixtures, amino acids and quaternary ammonium compounds.

17. The ointment or lotion according to claim 13, wherein the anti-flocculants comprise at least one selected from the group consisting of sodium citrate, sodium pyrophosphate, sodium sorbate, zwitterionic surfactants, (3-[(3-cholamidopropyl)-dimethylammonio]-2-hydroxy-1-propane sulphonate) [CHAPSO], (3-[(3-cholamidopro-pyl)-dimethylammonio]-1-propane sulphonate) [CHAPS], N-dodecyl-N,N-dimethyl-3-ammonio-1-propane sul-phonate, cationic surfactants, preservatives, benzyldimethylhexadecyl ammonium chloride, methyl-benzethonium chloride, benzalkonium chloride and cetylpyridinium chloride.

18. The ointment or lotion according to claim 9, further comprising at least one viscosity-increasing substance selected from the group consisting of methyl cellulose, hydroxyethyl cellulose, hydroxypropyl cellulose, sodium carboxymethylcellulose, polyvinyl derivatives, polyvinyl alcohol, polyvinyl-pyrrolidone, polyvinyl acetate, alginates, polyacry-lates, xanthans and pectins.

19. The ointment or lotion according to claim 13, wherein the stabilisers and anti-flocculants are contained in the dispersion in a concentration of from 0.001% to 30%.

20. A Method for producing an ointment or lotion comprising lipid particles comprising a matrix prepared from a blend of a) a lipid which is solid at 37° C. (solid lipid) or a mixture of such solid lipids, and b) a lipid which has a melting point below 4° C. (liquid lipid) or mixtures of such liquid lipids, wherein, at 20° C., the particles are definite particles possessing a particle matrix structure which is not completely in the polymorphic, stable β-modification, the particle matrix comprises a predominant fraction of liquid lipid or lipid in the liquid crystalline state (α-modification), such that the particle matrix is less ordered compared to the bulk material of the initial solid lipid, the crystallinity index being below the crystallinity index of the initial solid lipid is below 0.5, and the average particle size being in the nanometer range of 30 to 1000 nm (0.03 to 1.0 μm), the method comprising dispersing the lipids (as the inner phase) above their melting point in a liquid state in an outer phase (dispersion medium), cooling the dispersion to form the lipid particles, and the dispersion medium is optionally removed, wherein the liquid lipid, or a mixture of liquid lipids, and the solid lipid, or a mixture of solid lipids, are mixed in a proportion of from 80+20 to 0.1+99.9.

21. A Method for producing an ointment or lotion lipid particles comprising a matrix prepared from a blend of a) a lipid which is solid at 37° C. (solid lipid) or a mixture of such solid lipids, and b) a lipid which has a melting point below 4° C. (liquid lipid) or mixtures of such liquid lipids, wherein, at 20° C., the particles are definite particles possessing a particle matrix structure which is not completely in the polymorphic, stable β-modification, the particle matrix comprises a predominant fraction of liquid lipid or lipid in the liquid crystalline state (α-modification), such that the particle matrix is less ordered compared to the bulk material of the initial solid lipid, the crystallinity index being below the crystallinity index of the initial solid lipid is below 0.5, and the average particle size being in the nanometer range of 30 to 1000 nm (0.03 to 1.0 μm), the method comprising dispersing the lipids in the solid and/or partially solid state in an outer phase (dispersion medium) to form the lipid particles and the dispersion medium is optionally removed, wherein the liquid lipid, or a mixture of liquid lipids, and the solid lipid, or a mixture of solid lipids, are mixed in a proportion of from 80+20 to 0.1+99.9.

22. The method according to one of claim 20 or 21, characterised in that the lipids are dispersed by using high-pressure homogenisation, the lipid phase being added to the dispersion medium in one step or successively in sub-steps.

23. The method according to one of claim 20 or 21, characterised in that the lipids are dispersed by using flow machines based on the jet-stream principle, the lipid phase being added to the dispersion medium in one step or successively in sub-steps.

24. The method according to one of claim 20 or 21, characterised in that the lipids are dispersed by using stirrers, the lipid phase being added to the dispersion medium in one step or successively in sub-steps.

25. The method according to one of claim 20 or 21, characterised in that the lipids are dispersed by using static blenders on the microscale or macro-scale, the lipid phase being added to the dispersion medium in one step or successively in sub-steps.

26. The method according to one of claim 20 or 21, characterised in that the lipids are produced by using two or more in-series homogenizers, the lipid phase being added to the dispersion medium successively in sub-steps by dispersing one lipid fraction using a high-pressure homogeniser and subsequently dispersing the remaining lipid using a high-speed stirrer.

27. The ointment or lotion according to claim 9, wherein the dispersion has been converted into a dry product by removing an outer phase fraction by spray-drying or lyophilisation to thereby form an FDDS (fast dissolving delivery system) or lyophilisate for reconstitution before application.

28. The ointment or lotion according to claim 9, wherein the lipid particle dispersions are produced aseptically, sterilised and/or can be applied parenterally.

29. The ointment or lotion according to claim 1, loaded with natural, semi-synthetic and synthetic cyclosporins, for use on the skin and in the gastrointestinal tract.

30. The ointment or lotion according to claim 29, characterised in that the lipid matrix was produced by mixing lipids which are solid and liquid at room temperature (20° C.).

31. The ointment or lotion according to claim 1, further comprising mixing the lipid particles or lipid particle dispersion with a cream.

32. The ointment or lotion according to claim 1, wherein they contain natural, synthetic, semi-synthetic odoriferous substances individually or in a mixture, their isolated odoriferous substances, perfumes, pheromones or repellents.

33. The ointment or lotion according to claim 32, wherein they contain at least one selected from the group consisting of citrus oil, rose oil, lavender oil, bergamot oil, balm mint oil, clove oil, cinnamon oil, orange oil, jasmine oil, rosemary oil, aniseed oil, peppermint oil, sandalwood oil, ylang-ylang oil or their isolated constituents, 1,8-cineole, menthol, terpin hydrate, limonene, α-pinene and eugenol.

34. The ointment or lotion according to claim 32, wherein they contain at least one perfume.

35. The ointment or lotion according to claim 32, wherein they contain natural repellents, citrus oils, eucalyptus oil or camphor, or synthetic repellents.

36. The ointment or lotion according to claim 1, wherein they contain markers radioactive compounds, dyes, fluorescent dyes, iron oxides such as magnetite, small iron oxide particles in the approximately range approximately of 1 to 3 nm, individually or in mixtures.

37. The ointment or lotion according to claim 36, wherein they contain iodine isotopes, technetium isotopes, indium isotopes in the form of ions or as a component of molecules as the radioactive compounds.

38. The ointment or lotion according to claim 36, wherein they contain Sudan red as the dye and Nile red and fluorescein as the fluorescent dyes.

39. The ointment or lotion according to claim 1, wherein they contain lipids with sufficient change in the T1 and T2 relaxation time, for them to be used as a contrast medium in magnetic resonance tomography.

40. The ointment or lotion according to claim 1, wherein they contain poisons as active agents.

41. The ointment or lotion according to claim 40, wherein they contain chlorinated hydrocarbons, γ-hexachlorocyclohexane, pyrethrins, pyrethroids, alkyl phosphates, paraoxon, parathion, fenthion, dichlorvos and carbamates, butoxycarboxim, bendiocarb, methomyl or proxopur as the poisons.

42. The ointment or lotion according to claim 1, wherein the liquid oil is a compound of a short-chain (14 or fewer carbon atoms) fatty alcohol.

43. The ointment or lotion according to claim 1, wherein the oil is selected from the group consisting of isopropyl myristate, isopropyl palmitate, isopropyl stearate, octyldodecanol, isopropyl alcohol $C_{6-14}$ dicarboxylates, $C_{14-20}$ branched-chain, aliphatic fatty alcohols, $C_{6-14}$ fatty acid triglycerides and diglycerides, $C_{12-16}$ octanoates, and tridecyl salicylates.

44. The ointment or lotion according to claim 1, wherein the substance for solidifying the liquid oil is a lipid having a melting point above 40° C.

45. The ointment or lotion according to claim 1, wherein the solid lipid is selected from the group consisting of carnauba wax, hydroxyoctacosanyl hydroxystearate, Chinese wax, cetyl palmitate, beeswax or other waxes.

46. The ointment or lotion according to claim 1, further comprising am aqueous phase (dispersion medium) containing a gelling agent for thickening in that an aqueous phase is semi-solid owing to the use of a hydrophilic gelling agent whose yield point is above 5 Pa at 21° C. and whose gelling agents are selected from the group consisting of alginates, cellulose derivatives, xanthan gum, starch, starch derivatives, bentonites, glycerol monostearate, polyelectrolytic polymers, polyacrylic acids, carboxymethylcellulose and carrageenan.

47. The ointment or lotion according to claim 1, further comprising a stabiliser or stabilisers of the suspension are emulsifying agents selected from the group consisting of myristyl alcohol, cetyl alcohol, stearyl alcohol, polysorbates, sorbates, block polymers, poloxamers, glycerol fatty monoacid esters, glycerol monostearate, esters of polycarboxylic acids and fatty alcohols, or mono- and diglycerides of fatty acids esterified with lactic acid, citric acid, tartaric acid, and glycerol stearate citrate.

48. The ointment or lotion according to claim 1, wherein the components are produced at temperatures above 70° C. by using an inline rotor-stator mixer, a colloid mill or a high-pressure homogeniser.

49. The ointment or lotion according to claim 9, wherein the carrier system and the vehicle are produced together in one production process.

50. The ointment or lotion according to claim 9, wherein the active agent-containing lipid phase is first coarsely crushed, then comminuted, in particular ground, to the desired size, and finally the powdered lipid is admixed to a vehicle.

51. The ointment or lotion according to claim 41, wherein proportion is from 80+20 to 95+5.

52. The ointment or lotion according to claim 8, wherein the lipids comprise at least one selected from the group consisting of hard fat, glycerol trilaurate, glycerol myristate, glycerol palmitate, glycerol stearate or glycerol behenate), cetyl palmitate, carnauba wax or white wax (DAB) andr paraffin.

53. The ointment or lotion according to claim 11, wherein the outer phase is non-aqueous and contains liquid polyethylene glycols (PEG).

54. The ointment or lotion according to claim 12, wherein the outer phase comprises an oily or organic liquid selected from the group consisting of Miglyol oils, Miglyol 812, long chain triglycerides (LCT), soya oil, isopropyl myristate, castor oil, peanut oil, cottonseed oil, safflower oil, or other plant or semi-synthetic or synthetic oils, organic liquids, ethanol, isopropanol, butanol, octanol or other alcohols, esters, ethers and dimethyl sulphoxide.

55. The ointment or lotion according to claim 14, wherein the steric stabilisers and/or polymers comprise at least one selected from the group consisting of polyoxyethylene-polyoxypropylene block copolymers, ethoxylated fatty acid sorbates, polysorbates, ethoxylated mono- and diglycerides, ethoxylated lipids, ethoxylated fatty alcohols or fatty acids, and esters and ethers of sugars or sugar alcohols with fatty acids or fatty alcohols, sucrose monostearate, sucrose distearate, sucrose cocoate, sucrose stearate, sucrose dipalmitate, sucrose palmitate, sucrose laurate, sucrose octanoate, and sucrose oleate.

56. The ointment or lotion according to claim 13, wherein the surfactants comprise at least one selected from the group consisting of alkali metal soaps, metal soaps, calcium dilaurate, amine soaps, alkyl sulphates, alkyl sulphonates, mono- and diglycerides, fatty alcohols, cetyl alcohol, stearyl alcohol, fatty acids, fatty acid sorbates, span, esters and ethers of sugars or sugar alcohols with fatty acids or fatty alcohols, sucrose monostearate, sucrose distearate, sucrose cocoate, sucrose stearate, sucrose dipalmitate, sucrose palmitate, sucrose laurate, sucrose octanoate, sucrose oleate, natural surfactants, and saponins.

57. The ointment or lotion according to claim 13, wherein the charged ionic stabilisers comprise at least one selected from the group consisting of diacetyl phosphates, phosphatidyl glycerol, lecithins, egg lecithin, soya lecithin, chemically modified lecithins, hydrogenated lecithins, sphingolipids, sterols, cholesterol, cholesterol derivatives, stigmasterol, saturated and unsaturated fatty acids, bile acid salts, sodium cholate, sodium glycocholate, sodium taurocholate, sodium deoxycholate, amino acids and quaternary ammonium compounds.

58. The ointment or lotion according to claim 13, wherein the stabilisers and anti-flocculants are contained in the dispersion in a concentration of from 0.01% to 20% (m/m).

59. The ointment or lotion according to claim 6, wherein the active agents in the active agent-containing lipid particles comprise a cyclosporine, a UV blocker, a peptide, a protein, a hormone, titanium dioxide, or magnetite.

60. The ointment or lotion according to claim 32, wherein they contain N,N-diethyltoluamide (DEET), dibutyl phthalate, dimethyl phthalate or 2-ethyl-1,3-hexanediol.

61. The ointment or lotion according to claim 1, wherein a consistency of the dispersion has been increased by adding a gelling agent to the outer phase or an additional lipophilic phase.

62. The ointment or lotion according to claim 13, wherein the charged ionic stabilisers comprise at least one phospholipids.

63. The ointment or lotion according to claim 9 further comprising at least one viscosity-increasing substance selected from the group consisting of cellulose ethers and cellulose esters.

\* \* \* \* \*